United States Patent
Marle

(10) Patent No.: US 9,326,907 B2
(45) Date of Patent: May 3, 2016

(54) PATIENT POSITIONING AND SUPPORT SYSTEMS

(75) Inventor: Jason Marle, West Sussex (GB)

(73) Assignee: Varian Medical Systems, Inc., Palo Alto, CA (US)

(*) Notice: Subject to any disclaimer, the term of this patent is extended or adjusted under 35 U.S.C. 154(b) by 914 days.

(21) Appl. No.: 13/563,441

(22) Filed: Jul. 31, 2012

(65) Prior Publication Data

US 2014/0033432 A1 Feb. 6, 2014

(51) Int. Cl.
| | |
|---|---|
| *A61B 6/04* | (2006.01) |
| *A61G 7/10* | (2006.01) |
| *A61B 6/00* | (2006.01) |
| A61G 7/005 | (2006.01) |
| A61G 7/008 | (2006.01) |
| A61B 6/03 | (2006.01) |

(52) U.S. Cl.
CPC ............ *A61G 7/1057* (2013.01); *A61B 6/0407* (2013.01); *A61B 6/0457* (2013.01); *A61B 6/4494* (2013.01); *A61B 6/548* (2013.01); *A61B 6/03* (2013.01); *A61G 7/005* (2013.01); *A61G 7/008* (2013.01); *A61G 7/1017* (2013.01); *A61G 7/1044* (2013.01); *A61G 2210/50* (2013.01)

(58) Field of Classification Search
CPC ....... A61B 6/0407; A61G 13/04; A61G 13/06
USPC ......... 5/601, 607, 608, 610, 611; 378/20, 209
See application file for complete search history.

(56) References Cited

U.S. PATENT DOCUMENTS

| | | | | |
|---|---|---|---|---|
| 3,069,543 | A | * | 12/1962 | Sazavsky .......................... 5/601 |
| 5,013,018 | A | * | 5/1991 | Sicek et al. ...................... 5/601 |
| 6,502,261 | B1 | * | 1/2003 | Harwood ........................ 5/611 |
| 7,860,550 | B2 | * | 12/2010 | Saracen et al. ............... 600/410 |
| 8,160,205 | B2 | * | 4/2012 | Saracen et al. .................. 378/69 |
| 8,904,582 | B2 | * | 12/2014 | Bergfjord ......................... 5/601 |
| 2002/0092096 | A1 | | 7/2002 | Heimbrock |
| 2004/0133979 | A1 | | 7/2004 | Newkirk |
| 2005/0005356 | A1 | | 1/2005 | Zacharopoulos |
| 2006/0096029 | A1 | | 5/2006 | Osborne |
| 2006/0203958 | A1 | * | 9/2006 | Nagamine et al. .............. 378/20 |
| 2010/0275927 | A1 | | 11/2010 | Saracen |
| 2014/0034061 | A1 | | 2/2014 | Marle |

FOREIGN PATENT DOCUMENTS

| | | |
|---|---|---|
| DE | 102004013585 A1 | 10/2005 |
| WO | 2007018646 A1 | 2/2007 |

OTHER PUBLICATIONS

EPO, European Search Report in EP application No. 13178625 dated Sep. 14, 2015, 6 pages.

* cited by examiner

*Primary Examiner* — Fredrick Conley

(74) *Attorney, Agent, or Firm* — Houst Consulting

(57) ABSTRACT

A patient positioning system employs an arm having a first portion and a second portion which is telescopic relative to the first portion. A first positioning device may be coupled to the first portion of the arm providing support for the arm. The first positioning device is rotatable on a first axis, allowing the arm to rotate with the first positioning device. The second positioning device is coupled to the second portion of the arm and movable with the second portion of the arm relative to the first portion of the arm. The second positioning device is operable to rotate a patient support at least on a second axis.

35 Claims, 16 Drawing Sheets

PATIENT POSITIONING AND SUPPORT SYSTEMS

BACKGROUND

This disclosure relates generally to patient positioning and support systems useful in medical applications including radiation therapy and medical imaging, and in other applications.

Various patient positioning and support systems for radiation therapy, diagnostic imaging, or other medical procedures are known in the art. For radiation therapy, accurate positioning of patients is necessary to ensure accurate delivery of radiation doses to a treatment volume and to avoid overexposure of healthy tissue to high energy radiation. Accurate positioning of patients is also important in diagnostic imaging for determining the exact location of the treatment volume and other related information for treatment planning. Therefore, it would be desirable to provide a patient positioning system that can accurately position patients and allows correction of patient positions with full motion compatibility.

Imaging systems are increasingly used in radiation therapy e.g. to evaluate treatment results. For instance, images of magnetic resonance imaging (MRI) may provide good soft-tissue contrast of the patient anatomy. Images of X-ray imaging such as computed tomography (CT) may provide good contrast between bone density and soft tissue and have good spatial and temporal resolution. In some applications, a system including multiple imaging machines such as an MRI scanner and a CT scanner may be desirable to take the advantages provided by both imaging modalities. Therefore, it would be desirable to provide a patient positioning system that has sufficient range of movements and degrees of freedom in moving and positioning patients between a radiation treatment machine and an imaging machine, or between two or more imaging machines of different modalities.

Radiation therapy has developed to treat various diseases in a patient, including such as head and neck cancers, breast cancers, and prostate cancers etc. Structures for supporting a patient in treatment of brain cancers may be different from those in treatment of prostate cancers. Structures for supporting a patient in diagnostic imaging may also be different from those in radiation therapy partly due to the effects of different radiation energies on imaging and treatment. Therefore, it would be desirable to provide a patient support system that allows quick and easy changing of patient supports depending on required treatment or imaging, or depending on the location of the treatment volume in the patient.

SUMMARY

Patient positioning systems and methods are described herein. In some embodiments, the patient positioning system incorporates multiple degrees of freedom and provides improved accuracy of positioning. The positioning system can provide a minimal height significantly lower than those of conventional patient positioning systems to facilitate patient loading and unloading. For example, a minimum height of 550 mm or lower can be achieved. The travel range of the positioning system is also increased. A patient having a weight of 255 Kilograms or more can be safely supported by the positioning system. Patient positions can be remotely adjusted e.g. from the console area outside the treatment room in multiple degrees of freedom, thereby allowing accurate alignment of the treatment volume with the treatment beams. A positioning accuracy of 0.1 mm or smaller can be achieved using transducers or other feedback devices in the positioning system. Used in conjunction with a patient support system, the positioning system allows quick and easy changing of patient supports depending on required simulation or treatment. The capability of quick and easy changing of patient supports can significantly improve the workflow and safety when used with a collision management system. This allows the users to concentrate more on the patient rather than avoiding machine collisions.

Patient support systems are also described herein. The patient support systems may be used with the positioning systems described herein. The patient support systems may also be used with existing patient positioning systems. An interface structure may be mounted to a positioning system to allow multiple patient supports to be easily and quickly fitted. A detection system which can identify the patient support and feed this information to a control system can be integrated into the patient support system. Load cells which can measure the weight and center of gravity of the patient support and feed this information to a control system can also be integrated to the patient support system.

Overall, this disclosure provides a full solution to patient positioning and support. Other embodiments are further described herein.

BRIEF DESCRIPTION OF THE DRAWINGS

These and other features and advantages of the patient positioning and support systems will become better understood upon reading of the following detailed description in conjunction with the accompanying drawings and the appended claims provided below, where:

DETAILED DESCRIPTION

Figure 1:
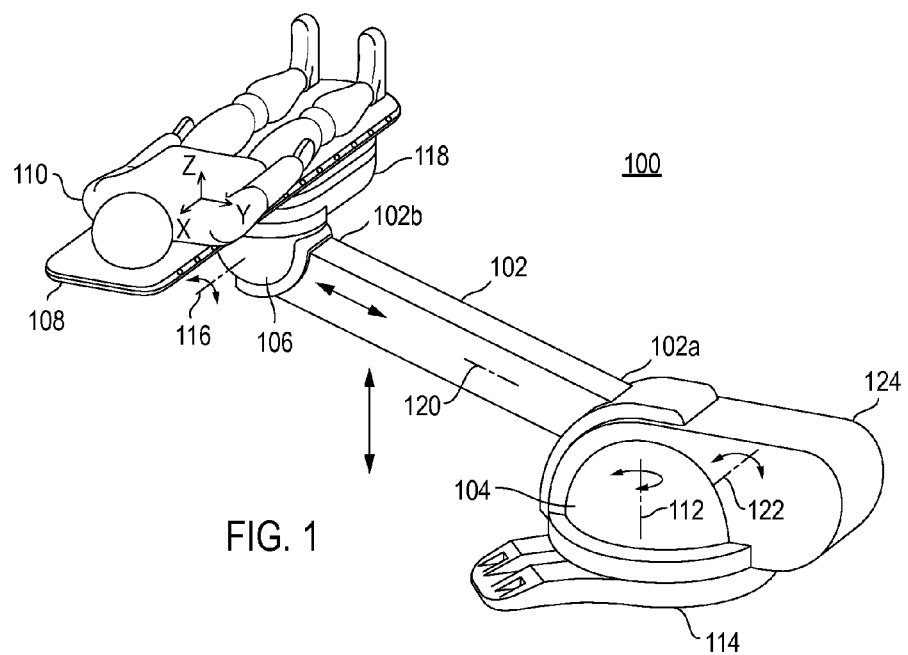
FIG. 1 illustrates an exemplary patient positioning system described herein.

Various embodiments of patient positioning systems and patient support systems are described. It is to be understood that the disclosure is not limited to the particular embodiments described as such which may, of course, vary. An aspect described in conjunction with a particular embodiment is not necessarily limited to that embodiment and can be practiced in any other embodiments. For instance, while various patient positioning and support systems are shown and described in conjunction with gantry-based X-ray treatment systems, it will be appreciated that the systems described herein can also be used with other medical systems or for other applications.

Definition

Various relative terms such as "upper," "lower," "vertical," "horizontal," "above," "under," "top," and "bottom," etc. may be used to facilitate description of various embodiments. The relative terms are defined with respect to a conventional orientation of a structure and do not necessarily represent an actual orientation of the structure in manufacture or use. The following detailed description is, therefore, not to be taken in a limiting sense.

As used in the description and appended claims, the singular forms of "a," "an," and "the" may include plural references unless the context clearly dictates otherwise. For example, reference to "a positioning device" may include one or more positioning devices. Reference to "the patient support" may include one or more patient supports having the features described.

As used herein, the term "patient" refers to any subject that can be supported or positioned by the patient support or patient positioning system described herein. The patient can be a human, animal, or any other objects of interest.

As used herein, the term "patient support" refers to a body or a body assembly which is configured to support a patient. The term "patient support" may be used interchangeably with the term "couch top."

As used herein, the term "patient positioning device" or "positioning device" refers to a device that is operable to move a patient support. By way of example, a positioning device may include an actuator that supplies energy and a transmission mechanism that transmits the energy for moving a patient support which is directly or indirectly coupled to the transmission mechanism. An actuator may include a motor, which may be an electric, a pneumatic, or a piezoelectric motor, etc. Other types of actuators such as hydraulic piston-cylinder systems may also be used. The term "patient positioning system" or "positioning system" may be used interchangeably with the term "couch" and may include one or more positioning devices described herein.

As used herein, the term "turret" refers to a rotatable body which includes an enclosure and one or more positioning devices in the enclosure. The enclosure may be in various suitable shapes such as a hemisphere or an approximate hemisphere, a portion of a sphere, a portion of sphere with an extension of any shape, and any other regular or irregular shapes.

As used herein, the term "telescopic" refers to a feature of an arm having at least two portions which can extend and/or retract relative to each other along a longitudinal axis of the arm.

As used herein, the term "articulated arm" refers to an arm that includes one or more rotary joints between the two end portions of the arm. The term "non-articulated arm" refers to an arm that does not include a rotary joint between the two end portions of the arm.

As used herein, the term "yaw" refers to a rotation of a patient support on an axis that is perpendicular to the patient support plane. The term "roll" refers to a rotation of a patient support on an axis that is in the patient support plane and parallel to the patient's head and toe orientation. The term "pitch" refers to a rotation of a patient support on an axis that is in the patient support plane and is perpendicular to the patient's head and toe orientation. For simplicity of description, an axis on which a patient support is caused to yaw, roll, or pitch may be referred to as a yaw-, roll-, or pitch-axis respectively.

Patient Positioning Systems

The patient positioning system described herein may include an arm having a first end portion and a second end portion, a first turret coupled to the arm first end portion, and a second turret coupled to the arm second end portion. The first turret provides support for the arm and is rotatable on a first axis, thereby allowing the arm to rotate as the first turret rotates. The second turret is supported by the arm and thus is movable by the arm. The second turret is rotatable on a second axis, thereby allowing a carriage or a patient support coupled thereto to rotate with the second turret. The second turret may also be operable to rotate a patient support or a carriage coupled thereto on an additional axis that is different from the second axis.

The patient positioning system may include a base member which is translatable and/or rotatable. The first turret may be coupled to the base member, and as such, the first turret may be further translated and/or rotated with the movable base member. In some embodiments, the patient positioning system may further include a carriage between the second turret and the patient support. The carriage may operate to move e.g. to translate a patient support and/or rotate a patient support on an axis.

The arm may be an elongate arm which can provide sufficient range of movements of the patient support. The arm may be a non-articulated arm, e.g., an arm that does not include any rotary joints between the first and second end portions. The arm may include a first portion and a second portion that is extendable or retractable relative to the first portion. The capability of extending and retracting of the arm allows the second turret and the patient support coupled to the second turret to travel in ranges, thereby increasing the flexibility and versatility of the positioning system. The arm may also be provided with the capability of pivoting on the first turret, thereby allowing the patient support coupled to the second turret to raise or lower its height relative to the ground.

As defined above, a turret is a rotatable body which includes an enclosure and one or more positioning devices inside the enclosure. The positioning system described herein, which includes a first turret and a second turret coupled to the end portions of an arm, presents a "look and feel" that is drastically different from the conventional patient positioning systems. It provides great versatility, flexibility, and accuracy in loading/unloading, transporting, and positioning patients for either treatment or imaging, or other procedures.

In some embodiments, a patient positioning system described herein may include an arm having a first portion and a second portion which is telescopic relative to the first portion. The arm may be a non-articulated arm. A first positioning device may be coupled to the first portion of the arm. A second positioning device may be coupled to the second portion of the arm. The first positioning device may provide support for the arm and is rotatable, thereby allowing the arm to rotate with the first positioning device. The first positioning device may also operate to pivot the arm, thereby allowing the second positioning device and a patient support coupled thereto to raise or lower its height. The second positioning device may be supported by the arm and may be operable to rotate a patient support coupled to the second positioning device. The second positioning device may include a wrist-like assembly, which is operable to rotate the patient support in multiple degrees of freedom. For example, the second positioning device may operate to yaw, pitch, and roll the patient support.

The various embodiments of the patient positioning systems described herein may be operated by a control system. The control system may include a controller and a user interface that allows a user to control the operation of the positioning system through the controller. The user interface device may include a remote control unit or a software module on a mobile device that allows the user to remotely control the operations of the positioning system. By way of example, the patient positioning system described herein may include various actuators which may be configured to drive the positioning system or move the patient support in various degrees of freedom. The controller may be coupled to the various actuators and control the operation of the actuators via a user interface device.

Patient Support Systems

The patient support systems described herein may include a first section configured for attachment to a positioning system and a second section removably coupled to the first section. The first section may provide an interface between the removable second section and the positioning system and provide support for the second section. The first section provides a first support surface and the second section provides a second support surface. A combined or continuous support surface may be formed when the second section is coupled to the first section. In some embodiments, the patient support system may include a third section which may be removably coupled to the first section at a side opposite the side to which the second section is interfaced. The third section provides a third supporting surface. A combined or continuous support surface may be formed when the third and the second support sections are coupled to the first section. One of ordinary skill in the art will appreciate that any additional support sections along the length of the patient support and/or any additional lateral support sections may be included for supporting tall and/or big patients. Any additional support such as one or more bars may be attached underneath any of the support sections in case of heavy patients.

The patient support system may include a latching mechanism that facilitates the coupling or removing of the second section to or from the first section. The latching mechanism may be any suitable mechanism that allows quick and easy changing of the second section. Suitable lathing mechanisms include complementary hook-bar members, complementary slot-protrusion members, and so on. The patient support system may also include an aligning mechanism that facilitates aligning of the second section with the first section. The aligning mechanism may include one or more protrusion members at an end of the second section, and one or more slots at an end of the first section. The protrusion members and the slot members may be configured so that the protrusion members can be properly received in the slots when the first and the second sections are coupled. Likewise, the patient support system may include an additional latching mechanism for the coupling or removing of a third section to or from the first section. The patient support may also include an additional aligning mechanism for the aligning of the third section with the first section.

The patient support system described herein or at least the second section and/or the third section of the patient support system may include index features along the longitudinal sides of the second and/or third sections. The index features may be in the form of notches or recesses etc. which may be configured to receive a locking member to which a restraining or immobilization device can be secured.

The patient support system described herein may include a detection system which is configured to identify the type of the second section and/or the third section. One example is RFID detection system. The patient support system may also include one or more load cells that are configured to measure the weight of the patient support including the patient.

The patient support described herein can be constructed from a material that includes carbon fiber composites, methacrylate plastics, solid foams of various materials, or aerogels etc. In some embodiments, at least the second and/or the third sections can be constructed from a material comprising carbon fiber. In some embodiments, at least the second and/or the third sections may be constructed solid from a material comprising carbon fiber. In some embodiments, at least the second and/or third sections may be constructed having a hollow interior with its outer surface reinforced with a thin and strong material comprising carbon fiber. In some embodiments, the hollow interior may be optionally filled with light materials such as foam. In some embodiments, at least the second and/or third sections or at least a region of the second and/or third sections may be constructed with a material having lowered radiation attenuation. In some embodiments, the second and/or third sections may be constructed with a material having lowered radiation attenuation and sufficient strength and resiliency to support a patient having certain weight. Materials with lowered radiation attenuation are known in the art.

Methods of Use

The patient positioning systems and patient support systems described herein may be used in any medical applications, including treatments, diagnostics, and other medical procedures. By way of example, the patient positioning system described herein may be used in a gantry-based or non-gantry based radiation treatment system. The patient positioning system may also be used in various imaging systems including such as X-ray imaging, MRI, ultrasound imaging, etc. The positioning system may be used to transport and position a patient in a system that includes both a treatment machine and an imaging machine, or in a system that includes two or more imaging machines of different modalities. In will be appreciated that the patient positioning systems may also be used in non-medical applications.

By way of example, the patient positioning system may be used to position a patient in a first medical system for a first application. After the first application is completed in the first medical system, the patient positioning system may be used to transport the patient from the first medical system to a second medical system. In the second medical system, the patient positioning system may be used to position the patient for a second application.

The first medical system may be a treatment system such as a radiation therapy system, a surgery operation system etc. The second medical system may be an imaging system such as an X-ray imaging system, an MRI system, an ultrasound system etc. The imaging data obtained by the second medical system can be used to evaluate the result of the prior treatment in the first medical system, or to determine a next treatment plan or modify the previously determined plan based on the effectiveness of the prior treatment. Using a same system for patient positioning in both applications is advantageous as it can reduce the risk of positioning errors caused by moving the patient from one positioning system to another. It also improves workflow by reducing patient set up time. Alternatively, the first medical system may be an imaging system such as an X-ray imaging system, an MRI system, an ultrasound system etc. The second medical system may be a treatment system such as a radiation therapy system, a surgery operation system etc. The imaging data obtained by the first medical system can be used in determining a treatment plan for the patient to be treated in the second medical system.

Alternatively, the first and the second medical systems may both be an imaging system but of different modalities. For example, the first medical system may be an X-ray imaging system and the second medical system may be an MRI system or an ultrasound system etc., or vice versa. Therefore, the patient positioning system described herein may allow a user to take the advantages offered by two or more imaging modalities without having to transfer the patient from one positioning system to another. By way of example, X-ray images can provide good contrast between bone density and soft tissue and have good spatial and temporal resolution. MRI images may provide good soft-tissue contrast of the patient anatomy.

The first and the second medical systems may be located in different rooms. The positioning system described herein can be used to transport the patient from a first room to a second room using e.g. a dedicated track or rails etc. Alternatively, the first and the second medical systems may be located in a same room and separated by a shielding structure. For example, a sliding door may be used to separate a radiation treatment machine from an MRI scanner to minimize the impact of radiation on the operation of the MRI scanner. Alternatively, no shielding structure is required to separate the first and second medical systems.

The patient positioning system described herein may also support a "pallet loading option" in which the patient on a patient support can be picked up by the positioning system from a gurney for treatment or imaging and returned to the gurney once the treatment or imaging is complete. For example, a patient may be set up on a patient support remotely outside the treatment room e.g. in a preparation room, and then transported into the treatment or imaging room using a transport system such as a gurney. Thanks to the flexibility and versatility of the patient positioning system described herein, the patient positioning system may position itself under the patient support and pick up the patient from the gurney. The patient positioning system may then move in multiple degrees of freedom to position the patient relative to the treatment or imaging machine. Once the treatment or imaging is complete, the positioning system may return the patient on the patient support to the gurney. The pallet loading option provided by the positioning system described herein can significantly improve the workflow and patient throughput.

Exemplary embodiments are now described with reference to the figures. It should be noted that some figures are not drawn to scale. The figures are only intended to facilitate the description of specific embodiments and are not intended as an exhaustive description or as a limitation on the scope of the invention.

FIG. 1 schematically illustrates an exemplary positioning system 100 of this disclosure. In general, the positioning system 100 includes an arm 102 having a first end portion 102a and a second end portion 102b, a first turret 104 coupled to the first end portion 102a, and a second turret 106 coupled to the second end portion 102b. A patient support 108 may be coupled to the second turret 106 for supporting a patient 110.

The first turret 104 provides support for the arm 102. The first turret 104 may rotate on a first axis 112, thereby allowing the arm 102 to rotate with the first turret 104. The first turret 104 may rotate clockwise and/or counterclockwise. For example, the first turret 104 may rotate in either or both directions in 180 degrees or greater. The first turret 104 may be coupled to a movable base member 114. The movable base member 114 may translate and/or rotate e.g. on a frame, a track, or a turntable etc., thereby allowing the first turret 104 to further translate, or rotate with the base member 114 on an additional axis. It should be noted that the frame, track, or the like may be installed on the ground, wall, or ceiling of a room, or on other supporting structures. As such, the first turret 104 may rotate on a first axis that is different from the vertical axis shown in FIG. 1.

The second turret 106 may be supported by the arm 102. As such, the second turret 106 and the patient support 108 coupled thereto may be moved by the arm 102. The second turret 106 may rotate on a second axis 116, thereby allowing the patient support 108 to rotate with the second turret 116. For example, the second turret 106 may rotate on the second axis 116 forwards in 40 degrees or greater and/or backwards in 10 degrees or greater. The rotation of the second turret 106 allows the patient support 108 to roll, pitch, or rotate on an axis depending on the orientation of the patient support as coupled to the second turret 106. By way of example, the patient support 108 may be oriented such that the longitudinal axis (x) of the patient support 108 may be parallel to the second axis 116. As such, a rotation of the second turret 106 on the second axis 116 may cause the patient support 108 to roll on x-axis. Alternatively, the patient support 108 may be oriented such that the longitudinal axis x of the patient support 108 may be perpendicular to the second axis 116. As such, a rotation of the second turret 106 on the second axis 116 may cause the patient 110 to pitch or tilt.

In some embodiments, the second turret 106 may further operate to yaw the patient support 108 on z-axis. For example, the second turret 106 may yaw the patient support 108 in either or both directions in 180 degrees or greater. The operation of the second turret 106 to yaw the patient support 108 on z-axis and the rotation of the second turret 106 on the second axis 116 allow the patient support 108 to rotate in all three degrees of freedom, as described above. In some embodiments, a carriage 118 may be provided between the second turret 106 and the patient support 108. The second turret 106 may operate to rotate the carriage 118 thereby causing the patient support 108 coupled to the carriage 118 to yaw on z-axis. The carriage 118 may include a plate member that is configured to interface with the patient support 108, as will be described in greater detail below. The carriage 118 may include one or more actuators that are operable to further move the patient support 108 as will be described in greater detail below.

The arm 102 may be a non-articulated arm, e.g., the arm 102 does not include any rotary joint between the first end portion 102a and the second end portion 102b. The rotation of the arm with the first turret allows the patient support to translate in a plane (x-y). Alternatively, the arm 102 may be an articulated arm including one or more rotary joints between the two end portions. The arm 102 may have two or more portions which are movable relative to each other along the longitudinal axis 120 of the arm 102. This may allow the arm 102 to extend and/or retract along the longitudinal axis 120, and thus allowing adjustment of the range of movements of the second turret 106 and the patient support 108. By way of example, the arm 102 may include a main arm portion supported by the first turret 104, and a telescopic arm portion coupled with the main arm portion. The telescopic arm portion may extend from or retract to the main arm portion along the longitudinal axis 120, thereby allowing the second turret 106 and the patient support 108 to travel farther away from or closer to the first turret 104. By way of example, the arm 102 may include a telescopic arm portion with a travel range of at least 300 mm or greater, or 400 mm or greater, or 600 mm or greater, or 1000 mm or greater.

In some embodiments, the arm 102 may be provided with a capability to pivot about the first turret 104. For example, the arm 102 may pivot clockwise or counterclockwise on an axis 122. Slot and bushing or similar structures may be provided in the first turret 104 to facilitate the pivoting of the arm 102. The pivoting of the arm 102 allows adjustment of the height of the patient support 108. For example, the arm 102 may pivot counterclockwise to lower the patient support 108 to a height of 600 mm or lower with respect to the ground, or 550 mm or lower, or 500 mm or lower. A lower minimal height of the patient support may be desirable in loading and unloading of a patient. The minimal height achieved by the positioning system 100 described herein is significantly smaller than the conventional systems. Conversely, the arm 102 may pivot clockwise to raise the patient support 108 to a height of 1950 mm or greater, which may be desirable in some applications.

Figure 2:
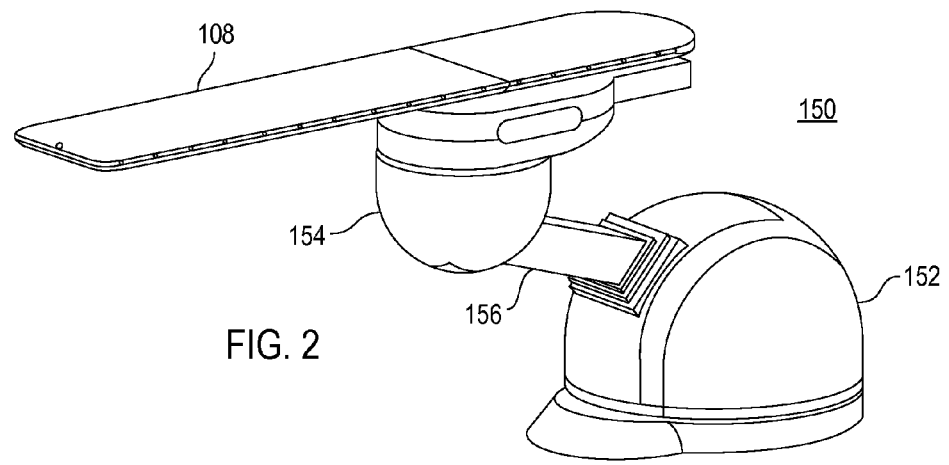
FIG. 2 illustrates another exemplary patient positioning system described herein.

The patient positioning system 100 described herein has a "look and feel" that is drastically different from conventional patient positioning systems. The first and second turrets 104, 106 may be in the shape of a hemisphere or an approximate hemisphere, a portion of a sphere, or a portion of sphere with an extension of any shape, or any other regular or irregular shapes. FIG. 2 shows an exemplary positioning system 150 which includes a first turret 152 and a second turret 154 each of which is in the shape of a portion of a sphere and coupled to an end portion of an arm 156. In the exemplary positioning system 100 shown in FIG. 1, the first turret 104 is in the shape of an approximate hemisphere with an extension 124 to provide the arm 102 with an extended travel capability and to provide an additional balance for the positioning system 100. The first turret 104 may have a spherical contour generally facing upward to provide a good balance for the positioning system 100. The second turret 106 may have a spherical contour generally facing downward to facilitate rotation of the turret at the second end portion of the arm.

The first and the second turrets 104, 106 may each enclose one or more positioning devices. A positioning device may include an actuator and an energy transmission mechanism, which may operate to move a patient support that is directly or indirectly coupled to the positioning device. For example, the first turret 104 may enclose an actuator which is operable to pivot the arm 102 on an axis 122. The first turret 104 may also enclose an actuator that is operable to rotate the turret 104 on the first axis 112. Alternatively, the actuator that operates to rotate the first turret 104 may be enclosed in the base member 114. In some embodiments, the first turret 104 may further enclose an actuator that is operable to extend and retract a telescopic arm portion of the arm 102. Alternatively, the actuator that operates to move the telescopic arm portion may be enclosed in the main arm portion, which may be supported by the first turret 104. The main arm portion or at least a portion of the main arm portion may be enclosed in the first turret 104. Inside the second turret 106 may be enclosed an actuator that is operable to rotate the turret 106 on the second axis 116. The second turret 106 may also enclose devices that are operable to rotate the patient support 108 or the carriage 118 which is coupled to the second turret 106.

Figure 3:
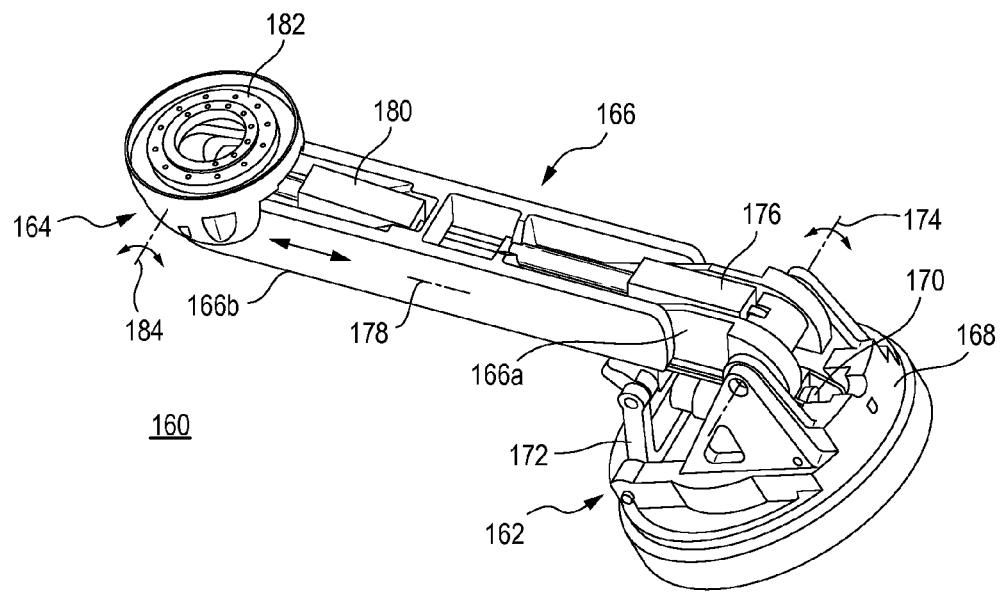
FIG. 3 is a cut-away view of an exemplary patient positioning system described herein.

FIG. 3 is a cut-away view of an exemplary patient positioning system 160 with a portion of the enclosures of the first turret 162, the second turret 164 and the arm 166 being removed to show some components inside. In the exemplary embodiment shown in FIG. 3, the arm 166 includes a main arm portion 166a and telescopic arm portion 166b. The main arm portion 166a is rotatably supported by a pedestal or base structure 168. An actuator 170 and a lift assembly 172 enclosed in the first turret 162 may operate to pivot the arm 166 on an axis 174. An actuator 176 enclosed in the main arm portion 166a may operate to extend and retract the telescopic arm portion 166b along the longitudinal axis 178 of the arm 166. An actuator 180 enclosed in the telescopic arm portion 166b may operate to rotate a geared bearing 182, causing a patient support or a carriage coupled thereto to rotate. While not shown in FIG. 3, an actuator may be enclosed in the second turret 164 to rotate the turret on the second axis 184.

Figure 4:
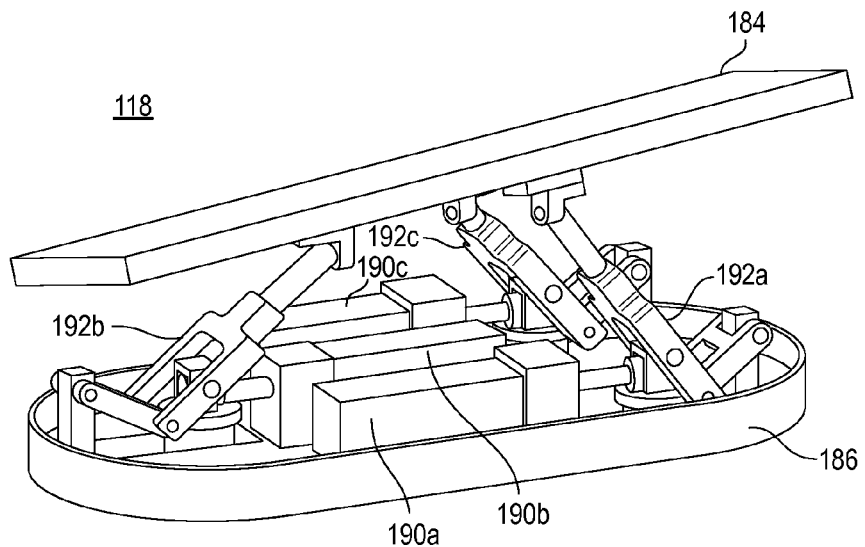
FIG. 4 is a cut-away view of a carriage that can be incorporated in the patient positioning system described herein.

FIG. 4 illustrates an exemplary carriage 118 that may be provided between the second turret and the patient support. The carriage 118 may include a plate member 184 configured to interface with a patient support and a base structure 186 configured to support components enclosed in the carriage 118. Bellows, bushings or the like which may be attached to the plate member 184 and the base structure 186 are removed in FIG. 4 to show the actuators, lift assemblies, and other components enclosed inside the carriage 118. The bellows, bushings or the like may provide an enclosure to shield the components inside the enclosure from radiation. Three actuators 190a, 190b, 190c and three lift assemblies 192a, 192b, 192c are shown although a different number of actuators and lift assemblies may be used. The actuators 190a, 190b, 190c may be electric motors or actuators using pneumatic or hydraulic pressures. Each of the actuators 190a, 190b, 190c may operate to drive one of the lift assemblies 192a, 192b, 192c to move the plate member 184 relative to the base structure 186. For example, a lift assembly 192a may include an upper lift member with an end coupled to the plate member 184 and a lower lift member with an end coupled to the base structure 186. The other ends of the upper and lower lift members may be rotatably coupled to a joint, which in turn may be coupled to the actuator 190a. The actuator 190a may operate to pull or push the joint to cause the upper and lower lift members to fold or expand, thereby generating a force to pull or push the plate member 184. The actuators 190b, 190c and lift assemblies 192b, 192c may operate in a manner similar to the actuator 190a and lift assembly 192a. The actuators 190a, 190b, 190c and lift assemblies 192a, 192b, 192c may operate coordinately to cause the plate member 184, and thus a patient support coupled to the plate member to move or rotate on an axis.

Figure 5A:
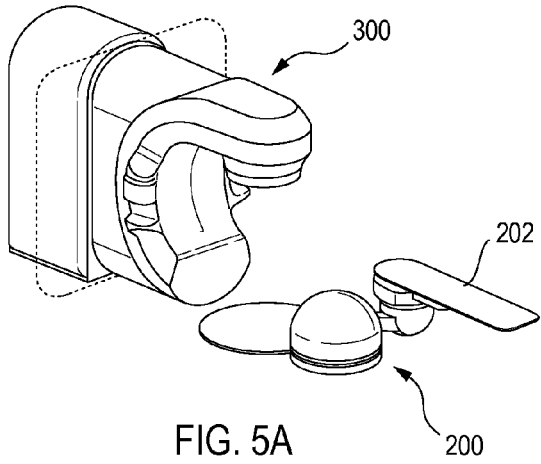
FIGS. 5A-5D illustrate an exemplary patient positioning system in a radiation treatment system according to some embodiments of the disclosure.
Figure 5B:
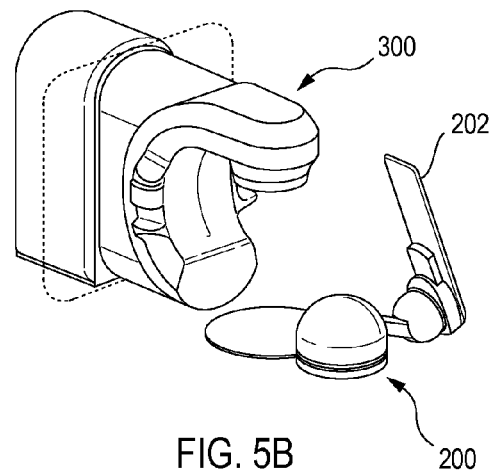
Figure 5C:
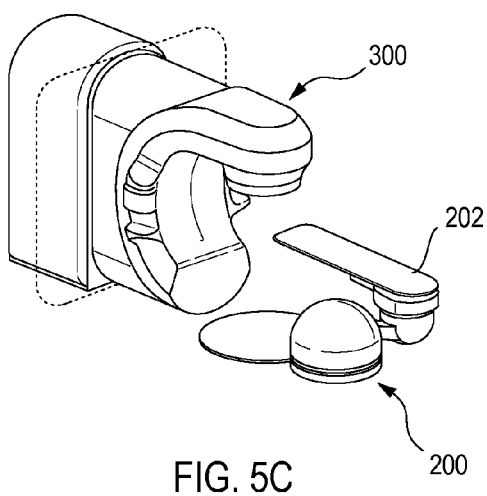
Figure 5D:
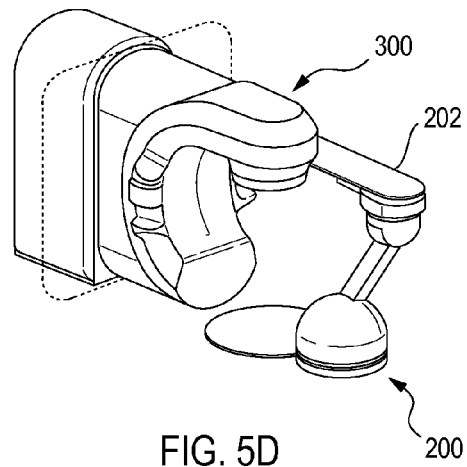

The patient positioning systems described herein provides full motion compatibility and great flexibility and versatility in positioning, loading, and unloading of patients. FIGS. 5A-5D illustrate an exemplary patient positioning system 200 used to position, load, and unload a patient (not shown) in a radiation treatment system 300. As shown in FIG. 5A, the patient positioning system 200 may significantly lower the height of the patient support 202 to facilitate loading and unloading of the patient in a horizontal manner. FIG. 5B shows that the patient positioning system 200 may readily change the orientation of the patient support 202 with respect to the radiation system 300 and/or the angle of the patient support 202 with respect to the ground to facilitate loading and unloading of a patient in a generally standing or leaning manner. Once the patient is loaded and secured on the patient support 202, the patient positioning system 200 may move the patient support 202 in multiple degrees of freedom to position the patient to a desired position with respect to the radiation system 300. FIG. 5C shows the patient positioning system 200 and the patient support 202 in a treatment position. FIG. 5D shows the height of the patient support 202 that can be achieved by the positioning system 200 described herein.

Figure 6A:
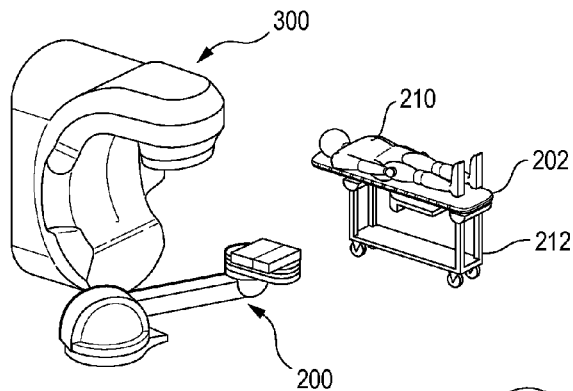
FIGS. 6A-6D illustrate an exemplary patient positioning system in a radiation treatment system according to some other embodiments of the disclosure.
Figure 6B:
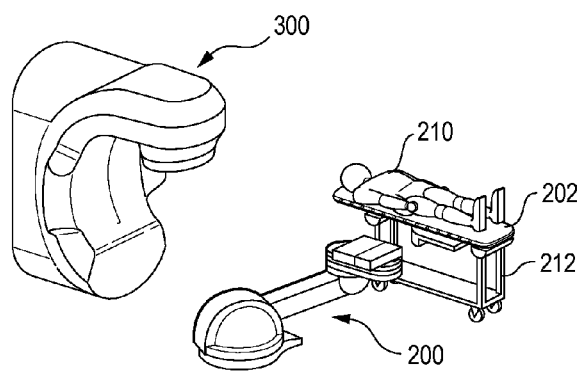
Figure 6C:
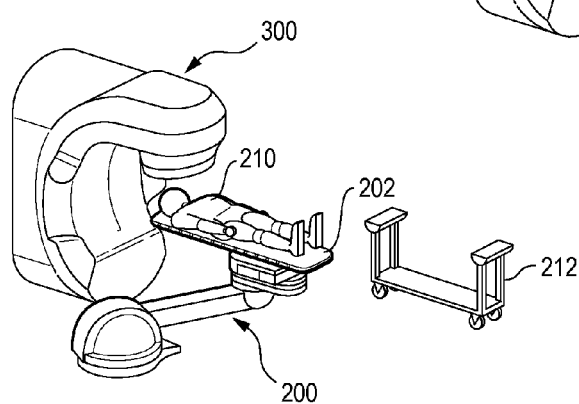
Figure 6D:
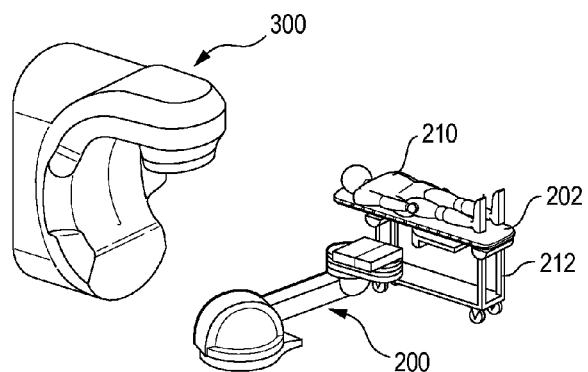

Advantageously, the patient positioning system described herein supports a "pallet loading option" in which a patient on a patient support can be picked up by the positioning system from a gurney for treatment or imaging and returned to the gurney once the treatment or imaging procedure is complete. The pallet loading option provided by the positioning system described herein can significantly improve the workflow and patient throughput, as illustrate by FIGS. 6A-6D. The patient 210 can be set up on a patient support 202 remotely outside the treatment room e.g. in a preparation room. Once the patient 210 has been set up, it can be transported into the treatment room using a transport system such as a gurney or the like 212 (FIG. 6A). The patient positioning system 200 may move to the gurney 212 and position itself under the patient support 202 by e.g. rotating the lower turret, extending or retracting the arm, or pivoting the arm up or down etc. The positioning system 200 can then pick up the patient 210 on the patient support 202 from the gurney 212 (FIG. 6B). A suitable mechanism may be used to secure the patient support 202 on the positioning system 200. Once the patient support 202 is secured, the patient positioning system 200 may then move in multiple degrees of freedom, as described above, to position the patient 210 relative to the radiation system 300 (FIG. 6C). Once the treatment is complete, the positioning system 200 may return the patient 210 on the patient support 202 to the gurney 212 (FIG. 6D).

Figure 7:
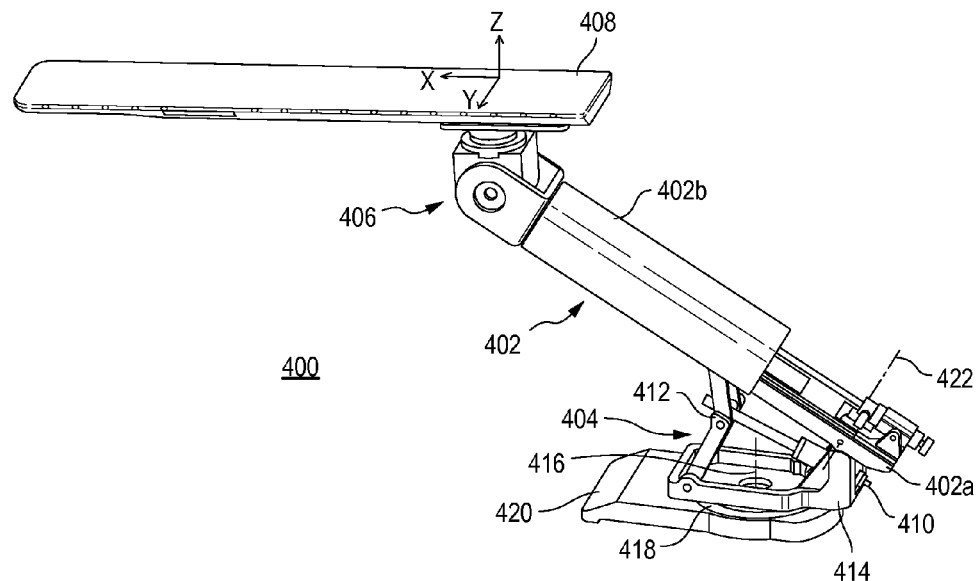
FIG. 7 illustrates a further exemplary patient positioning system described herein.

FIG. 7 illustrates a further exemplary positioning system 400 of this disclosure. In general, the patient positioning system 400 may include an arm 402 having a first arm portion 402a and a second arm portion 402b which is telescopic relative to the first arm portion 402a. A first positioning device 404 may be coupled to the first arm portion 402a. A second positioning device 406 may be coupled to the second arm portion 402b. A patient support 408 may be coupled to the second positioning device 406 for supporting a patient.

The first positioning device 404 may include an actuator 410, a lift assembly 412, and a pedestal or base structure 414 supporting the actuator 410 and the lift assembly 412. The pedestal 414 may be rotated on a first axis 416, thereby causing the first positioning device 404 to rotate on the first axis 416. The rotation of the pedestal 414 can be effectuated by a rotary gear assembly 418 driven by an actuator (not shown in FIG. 7). The actuator that operates to drive the rotary gear assembly 418 may be located in a base member 420, which in turn can be translated or rotated by a turntable, on a frame or a track etc. The actuator that operates to drive the rotary gear assembly 418 may also be mounted on the pedestal 414.

Figure 8:
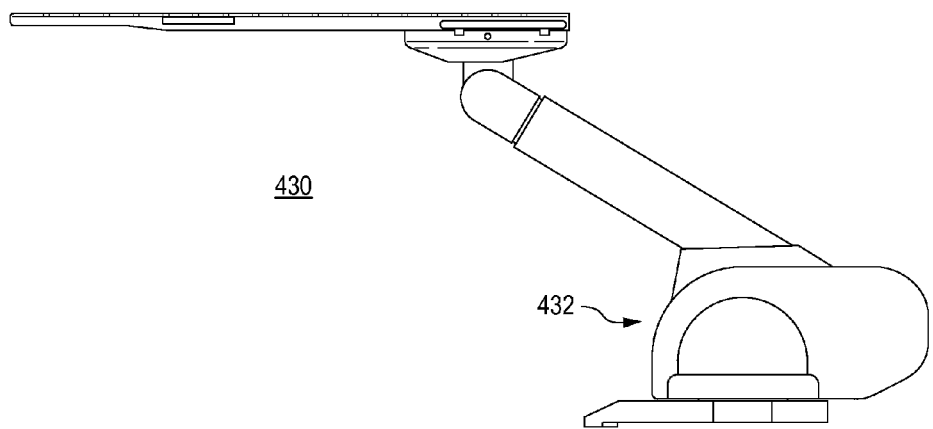
FIG. 8 illustrates a further exemplary patient positioning system described herein.

The first positioning device 404 provides support for the arm 402. For example, the first arm portion 402a may be supported by the lift assembly 412 and the pedestal 414. The actuator 410 and the lift assembly 412 may operate to pivot the first arm portion 402a on an axis 422, as will be described in greater detail below. In some embodiments, an enclosure or a cover in a suitable shape (not shown in FIG. 7) may enclose the actuator 410, lift assembly 412, and other components to shield the components from radiation. In some embodiments, the enclosure or cover may enclose the first arm portion 402a or at least a portion of the first arm portion 402a. Suitable bellows or the like and slot in the enclosure may be provided to allow the pivotal movement of the first arm portion 402a. FIG. 8 shows a positioning system 430 which includes an enclosure or cover 432 enclosing the first positioning device inside.

Figure 9A:
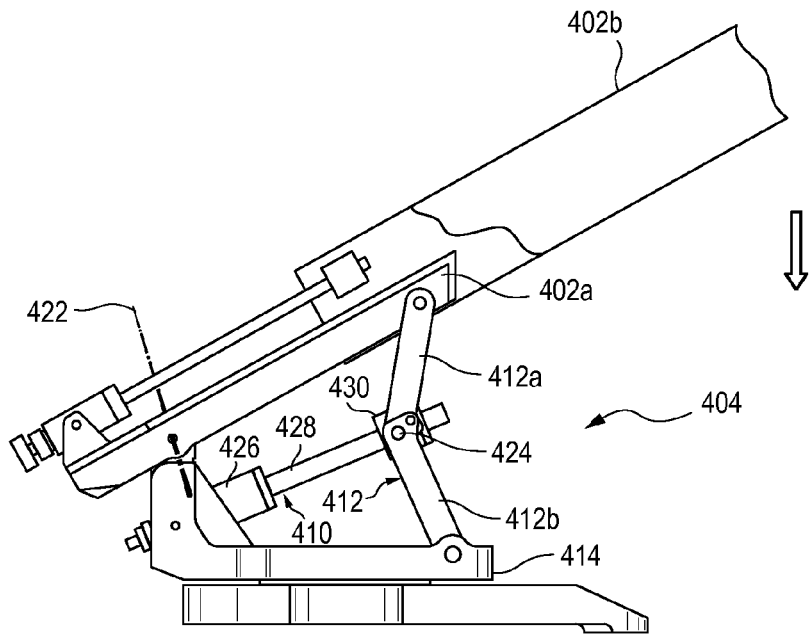
FIGS. 9A-9C illustrate an exemplary positioning device and the operation of the device according to some embodiments of the disclosure.
Figure 9B:
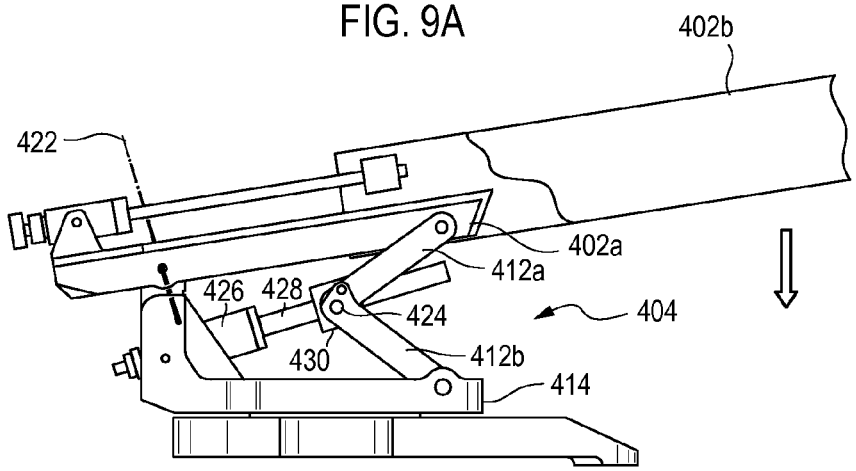
Figure 9C:
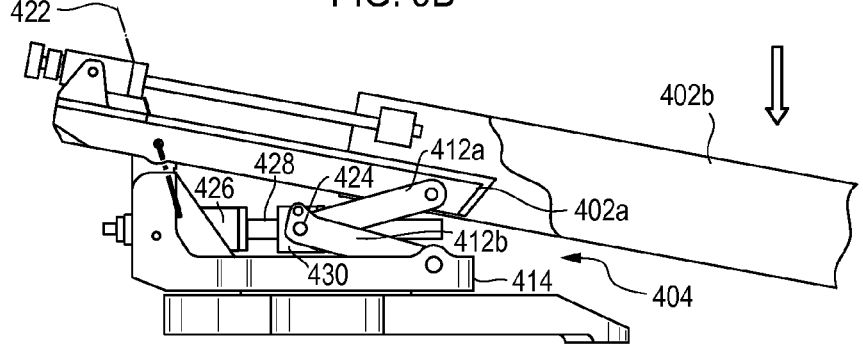

FIGS. 9A-9C illustrate the construction and operation of an exemplary first positioning device 404 with greater details. As shown, the first positioning device 404 includes an actuator 410 and a lift assembly 412 supported by a pedestal 414. The lift assembly 412 may include an upper lift 412a and a lower lift 412b. The upper lift 412a and lower lift 412b may be in the form of an arm, a fork or any other suitable configurations. The upper lift 412a may include a first end or ends connected to the first arm portion 402a. The lower lift 412b may include a first end or ends connected to the pedestal 414. The second end(s) of the upper lift 412a and the second end(s) of the lower lift 412b may be rotatably coupled to a joint 424. The actuator 410 may include a motor 426, a lead screw 428, and a nut 430. The motor 426 serves to rotate the lead screw 428, which engages the nut 430 and converts a rotary motion of the screw into a linear motion of the nut. The nut 430 may be coupled to the joint 424 which couples the upper and lower lifts 412a, 412b. Therefore, when the motor 426 actuates, the nut 430 may be caused to move e.g. in a direction towards the motor 426. This movement of the nut 430 may pull the joint 424 towards to the motor 426, causing the upper and lower lifts 412a, 412b to fold. The folding the upper and lower lifts 412a, 412b allows the arm 402 to pivot on the axis 422 clockwise or downwards. To pivot the arm 402 counterclockwise or upwards, an opposite procedure may be performed. For example, the lead screw 428 may cause the nut 430 to move in a direction that pushes the joint 424 away from the motor 426, causing the upper lift 412a and lower lift 412b to expand. The expanding of the upper and lower lifts 412a, 412b allows the arm 402 to pivot on the axis 422 counterclockwise or upwards.

The above description of the first positioning device 404 including an actuator 410 and a lift assembly 412 is provided for illustrative purpose. It will be appreciated by one of ordinary skill in the art that other types of actuators and energy transmission mechanisms may be used. For example, instead of or in addition to using electrical motors, actuators using pneumatic and hydraulic pressures in conjunction with pistons and cylinders etc. may be used. Structures or configurations that are different from the above described lift assembly may be used. A different number of lift arms or sections may be used to facilitate pivoting of the arm. Indeed, any suitable actuators and lift mechanisms may be used to effect the pivoting the arm 402 on the axis 422.

The first positioning device 404 and other positioning devices described herein may include various feedback devices or sensors to provide feedback signals to a control system to be described in greater detail below. The control system may determine or calculate the actual positions of the feedback devices or components to which the feedback devices are coupled based on the feedback signals. By way of example, one or more encoders may be coupled to a servo motor which effects pivoting of the arm. The servo motors and the encoders may be coupled to the control system, which may receive signals from the encoders and calculate the positions of the motors based on the signals received. The control system may then generate commands to the servo motors to correct the position e.g. of the arm if it differs from the desired location. Various feedback devices can be used including encoders, resolvers, Hall sensors, tachometers and potentiometers which are known in the art and commercially available. The patient support 408 may also be provided with various feedback devices or sensors which may transmit position signals to the control system for determination of position and/or motion of the patient support 408.

The pivoting of the arm 402 allows the positioning system 400 to raise or lower the height of the patient support 408. By way of example, a couch height of 1950 mm from the top of the patient support to the ground was achieved when the upper lift 412a and lower lift 412b were expanded to a scissor angle of 146.6° (FIG. 9A). A couch height of 1300 mm was achieved at a scissor angle of 72.4 degrees (FIG. 9B). A couch height of 650 mm was achieved when the upper lift 412a and the lower lift 412b were folded to a scissor angle of 27.3 degrees (FIG. 9C). With a proper actuator and lift mechanism, the positioning system 400 can raise a patient support from a height of 650 mm to a height of 1950 mm in 60 seconds or less, or 50 seconds or less, or 30 second or less.

Figure 10A:
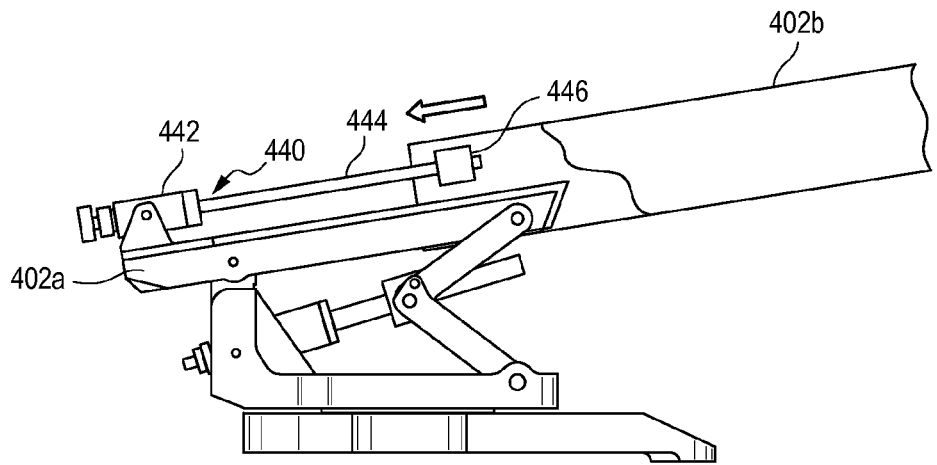
FIGS. 10A-10C illustrate another exemplary positioning device and the operation of the device according to some embodiments of the disclosure.
Figure 10B:
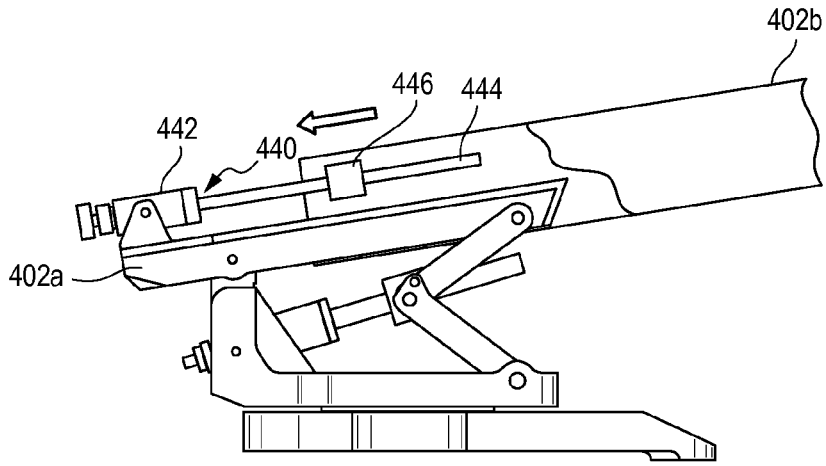
Figure 10C:
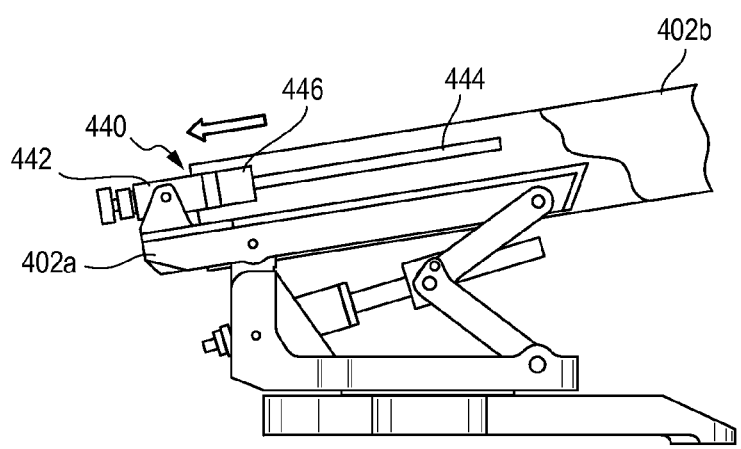

FIGS. 10A-10C illustrate an exemplary positioning device 440 which is operable to extend and retract the second arm portion 402b relative to the first arm portion 402a. The positioning device 440 may include a motor 442, a screw 444, and a nut 446. The motor 442 may be mounted on the first arm portion 402a. The nut 446 may be supported by a mount which in turn may be mounted on the second arm portion 402b. The motor 442 serves to rotate the screw 444, which engages the nut 446 and converts a rotary motion of the screw into a linear motion of the nut. Therefore, when the motor 442 actuates, the nut 446 may be caused to move e.g. in a direction towards the motor 442. This movement of the nut 446 may pull the second arm portion 402b towards to the motor 442 as indicated by the arrow, causing the second arm portion 402b to retract relative to the first arm portion 402a. Rails, guides, rollers, bearings, or other suitable mechanisms may be provided to the first arm portion and the second arm portion to facilitate the relative movement between the first and second arm portions. To extend the second arm portion 402b, an opposite procedure may be performed. For example, the screw 444 may cause the nut 446 to move in a direction away from the motor 442, causing the second arm portion 402b extend relative to the first arm portion 402a.

The above description of the exemplary positioning device 440 including the specific motor, screw and nut components is provided for the purpose of illustrating the relative movements of the first and the second arm portions 402a, 402b. It will be appreciated by one of ordinary skill in the art that other types of actuators including pneumatic and hydraulic actuators etc. may be used to effect the relative movements of the first and second arm portions 402a, 402b. The relative movement of the first and second arm portions 402a, 402b allows the positioning system 400 to adjust the range of the movements of the patient support 408. It also allows the positioning system 400 raise or lower the height of the patient support 408 when the lift assembly 412 forms a particular scissor angle. By way of example, at a given scissor angle of 72.4°, an extension of the second arm portion 402b by 600 mm may allow the positioning system to raise the couch height to 1300 mm (FIG. 10A). An extension of the second arm portion 402b by 300 mm may allow the positioning system 400 to raise the couch height to 1254.5 mm (FIG. 10B). A full retraction of the second arm portion 402b may allow the positioning system 400 to lower the couch height to 1209 mm (FIG. 10C).

Returning to FIG. 7, the patient positioning system 400 may include a second positioning device 406 coupled to the second arm portion 402b. The second positioning device 406 is operable to rotate the patient support 408 on at least one axis. In some embodiments, the second positioning device 406 may include a wrist assembly. In some embodiments, the wrist assembly may include actuators that are operable to yaw, roll, and pitch the patient support in multiple degrees of freedom.

Figure 11:
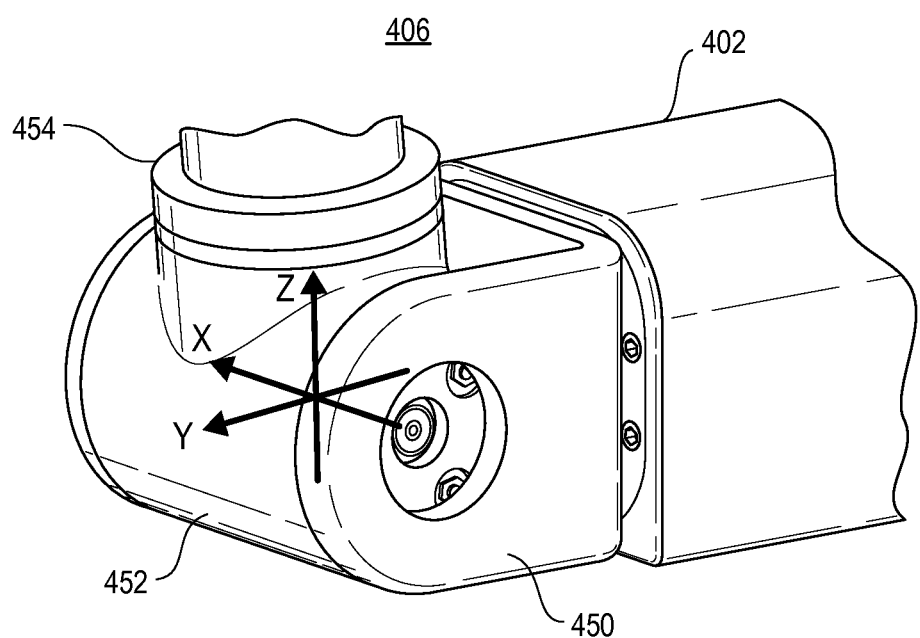
FIG. 11 illustrates an exemplary wrist assembly according to some embodiments of the disclosure.

FIG. 11 illustrates an exemplary wrist assembly which may be used as the second positioning device 406 of this disclosure. The wrist assembly 406 may include a first wrist 450 which can rotate on y-axis, a second wrist 452 which can rotate on x-axis, and a third wrist 454 which can rotate on z-axis. The first wrist 450 may be coupled to the arm 402. The second wrist 452 may be supported by the first wrist 450. The third wrist 454 may be coupled to the patient support 408. Therefore, the wrist assembly 406 may operate to rotate a patient support in all three degrees of freedom. By way of example, when the patient support 408 is in an orientation generally in-line with the arm 402 of the positioning system 400, as shown in FIG. 7, a rotation of the first wrist 450 on y-axis may cause the patient support 408 to roll; a rotation of the second wrist 452 on x-axis may cause the patient support 408 to pitch or tilt, and a rotation of the third wrist 454 on z-axis may cause the patient support 408 to yaw. By way of example, the first wrist 450 may rotate on y-axis both clockwise and counterclockwise, e.g. both in 30°. The second wrist 452 may rotate on x-axis both forward and backward, e.g. 40° forward or 10° backward. The third wrist 454 may rotate on z-axis both clockwise and counterclockwise e.g. both in 180°. It will be appreciated by one of ordinary skill in the art that the rotation degrees of the wrists can be readily modified depending on specific applications and this disclosure is not limited to the specific examples.

The wrist assembly 406 may include actuators which are constructed and/or configured to operate each of the first, second, and third wrists 450, 452, 454. By way of example, a motor of a suitable power and a gearbox of a suitable gear ratio may be provided inside an end portion of the arm 402 and configured to rotate the first wrist 450 on y-axis. A motor and a gearbox may be provided in the second wrist 452 enclosure and configured to rotate the second wrist 452 on x-axis. A motor and a gearbox may be provided under the patient support 408 and configured to rotate the third wrist 454 on z-axis. Motors and gearboxes are generally known in the art and commercially available. Therefore, detail description of their constructions and operations are omitted herein in order to not obscure the description of this disclosure. In general, gearboxes with suitable gear ratios may be chosen to provide suitable output torques or speeds for specific applications. In an exemplary embodiment, a gearbox having a gear ratio of 153 was chosen for the first and second wrists 450, 452, and a gearbox having a gear ratio of 135 chosen for the third wrist 454, which were sufficient to support a total load (including a patient and a couch top etc.) of more than 500 pounds. Gearboxes having different gear ratios may also be used depending on specific applications. Encoders and resolvers etc. may be included in the wrist assembly to provide feedback information on the positions and/or velocities of the motors or loads or other parts of the wrist assembly 406.

The positioning systems described herein enable the patient support 408 to move in multiple degrees of freedom, including yaw-, roll-, pitch-rotations and translations in x-, y-, and z-directions. The capability of moving a patient support in multiple degrees of freedom greatly aids in positioning of a patient in a treatment or an imaging system quickly and accurately. It allows the patient to be treated or imaged in different orientations and configurations and allows matching of patient position and/or orientation from session to session such as from a treatment session to an imaging session or vice versa, from a first treatment session to a second treatment session, or from a first imaging session to a second imaging session, etc. With a control system to be described in greater details below, the patient positioning systems described herein also allow adjustment or correction of patient positions during treatment or imaging e.g. during the delivery of radiation to the patient. Therefore, instead of or in addition to modifying an angle or a position of a radiation source, the positioning systems of this disclosure can be used to adjust the position or orientation of the patient in multiple degrees of freedom in executing a treatment plan. For example, a roll-rotation of the patient support based on a treatment plan may allow a target volume in the patient to be treated from different angles. A roll-rotation may also be used to compensate for slippage of a radiation source. The pitch- and/or yaw-rotations may provide for non-coplanar treatment fields. The positioning systems of this disclosure also allow loading and unloading of a patient in a more convenient manner.

Figure 12A:
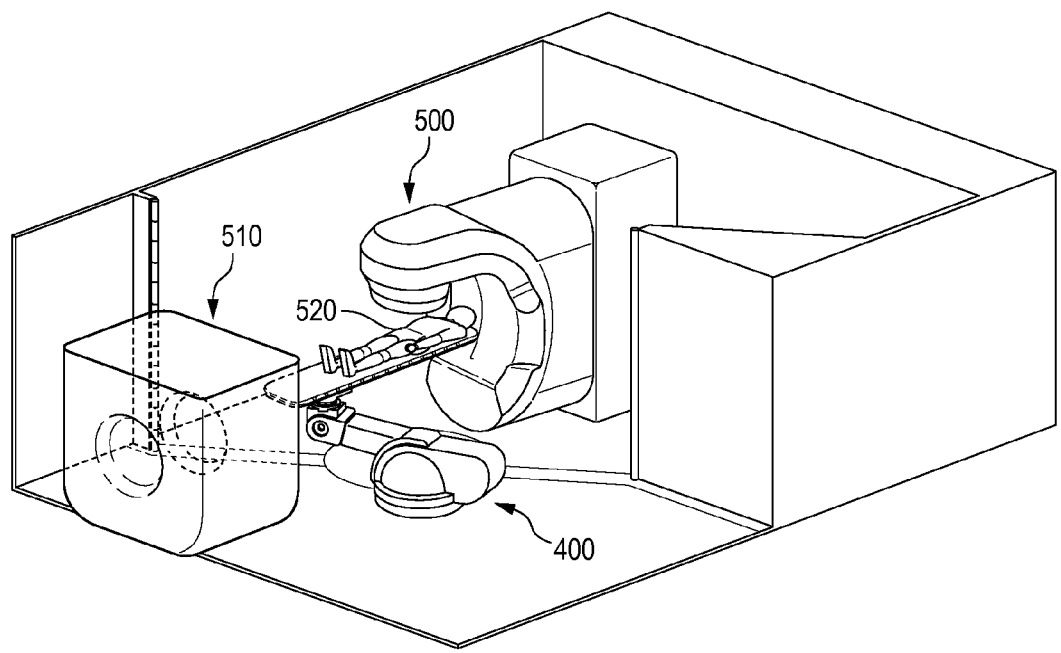
FIGS. 12A-12B illustrate an exemplary patient positioning system described herein in a system that includes a radiation treatment machine and an MRI scanner according to some embodiments of the disclosure.
Figure 12B:
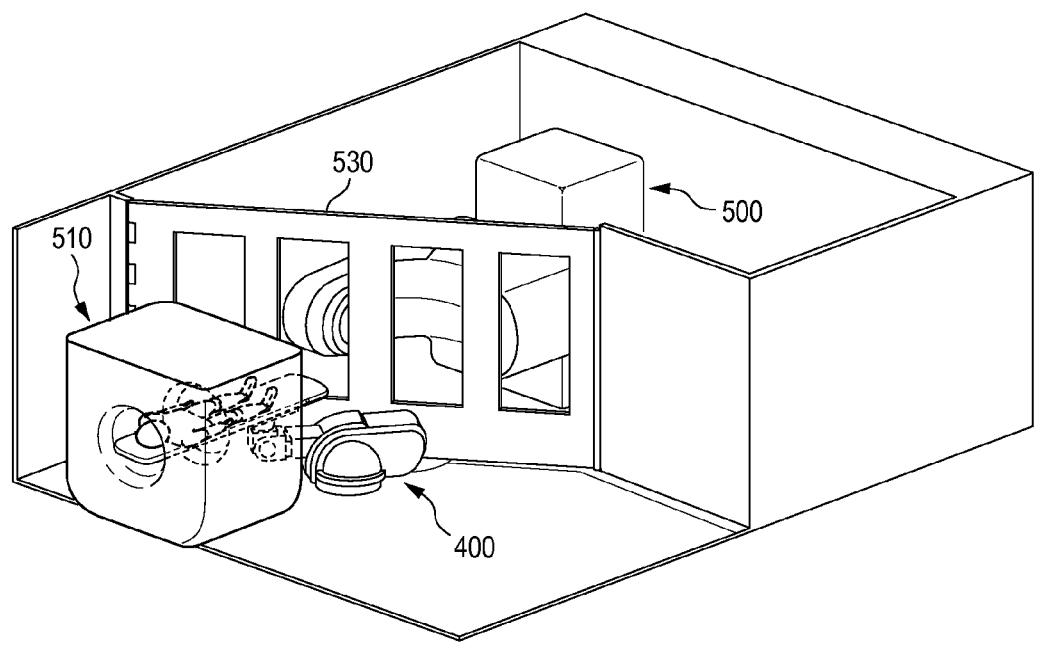
Figure 13:
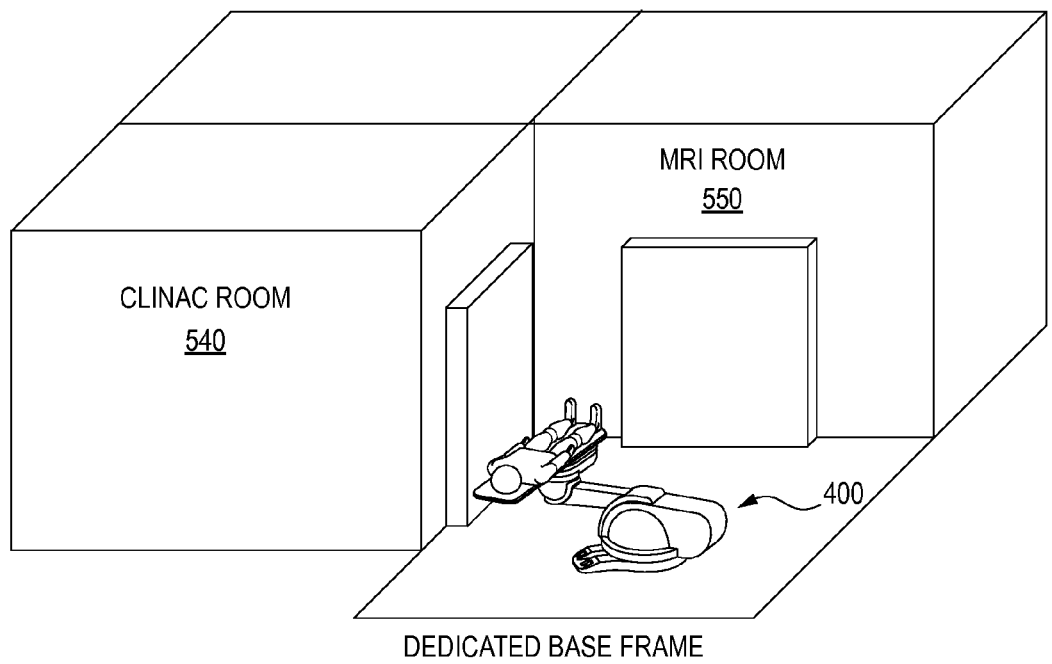
FIG. 13 illustrates an exemplary patient positioning system described herein in transporting a patient between a treatment room and an imaging room according to some embodiments of the disclosure.

The versatility and the range of movements of the patient positioning systems described herein make it useful in positioning a patient in a system that includes both a treatment machine and one or more imaging machines, or in a system that includes two or more imaging machines of different modalities. FIGS. 12A-12B show a room that includes both a radiation treatment machine 500 and an imaging machine such as an MRI scanner 510. The rotation capability and the range of travel motion of the positioning system 400 allow the use of the same positioning system 400 to position a patient 520 in both the treatment machine 500 and the imaging machine 510. The imaging data obtained by the imaging machine 510 can be used to evaluate the result of the prior treatment, or to determine a next treatment plan or modify the previously determined plan based on the effectiveness of the prior treatment. Using a same system for patient positioning in both a treatment machine and an imaging machine is advantageous as it can reduce the risk of positioning errors caused by transferring the patient from one positioning system to another. It also improves workflow by reducing patient set up time. A shielding structure such as a sliding door 530 may be provided to separate the MRI machine 510 from the treatment machine 500. The sliding door 530 may be retracted during treatment or during transport of the patient from the treatment system 500 to the MRI system 510. The sliding door 530 may be closed when the patient is positioned in the MRI system 510 to reduce the impact of radiation on the operation of the MRI system 510. In alternatively embodiments, a shielding structure such as a door 530 may not be required to separate a treatment machine from an imaging machine such as an X-ray imaging machine. As such, the treatment machine and the imaging machine can be located in the same room in any configurations. FIG. 13 shows that the patient positioning system 400 described herein can be used to serve two or more rooms, allowing transporting and positioning of a patient between a treatment room 540 and an imaging room 550 using a dedicated a frame, rail, track, or the like. The frame, rail, or track may be in any suitable configurations such as linear, arc, or linear and arc combination, depending on specific applications.

The operation of the patient positioning system described herein may be controlled by a control system. The control system may include a controller and a user interface that allows a user to control the operation of the positioning system through the controller.

The user interface may include an input device such as a keyboard, a mouse, a keypad, a touch screen or the like for inputting data or commands, and an output device such as a monitor for displaying information. In some embodiments, the user interface devices may be located outside the treatment room so that the user can control the operation of the positioning system remotely outside the treatment room. In some embodiments, the user interface may include a handheld unit or a remote control unit. The remote control unit may include functional buttons or icons on a touch screen that allow a user to select in controlling the operation of the positioning system. By way of example, the remote control unit may include functional buttons or icons that effect power "on or off" of the positioning system. The remote control unit may also include an emergency button or icon which when effected, allows shutdown of the positioning system. Other functional buttons or icons may include those that effect pivoting of the arm, extending or retracting of the arm, rotating of the first turret or first positioning device, and various motions of the second turret or the second positioning device, and so on.

The controller may include a memory and a processor such as a digital signal processor (DSP), a central processing unit (CPU), or a microprocessor (μP). The memory stores programs or algorithms including servo loop control algorithms and other programs for operation of various motion axes or positioning devices in the positioning system. Dimensional data of fixed structural features or hardstops in a coordinate system may be provided to the controller and stored in the memory. Treatment plan information may also be provided to the controller and stored in the memory. Treatment plan information may include the position of the target volume in the patient relative to the treatment machine or in a coordinate system, and the type and/or the amount of movement of the patient support during the procedure, etc. The processor may execute programs and generate commands for the operation of the positioning system.

The controller may be constructed and/or programmed to control the type and/or the amount of movements of the positioning system. For example, the controller may be configured to control the amount of rotation of the first turret, the amount of extension or retraction of the telescopic arm, the amount of pivoting of the arm on the first turret, and the amount of yaw-, roll-, or pitch-rotations of the patient support, and so on. The movements of the various motion axes may be prescribed in the treatment plan which may have been determined during a diagnostic session. Modified movement of various motion axes can also be made when the controller determines that the actual position of the patient support differs from the desired position prescribed in the treatment plan. The controller may be programmed to adjust or correct the position of the patient support so that the treatment volume in the patient remain properly aligned with respect to a radiation source throughout the treatment or imaging procedures.

The controller may be constructed and/or programmed to receive signals from feedback devices and calculate the position of the patient support or other parts of the positioning system in a coordinate system based on the feedback information from the feedback devices. The controller may be constructed and/or programmed to execute a servo loop algorithm such as a position control, torque control, velocity control etc., and modify the current or voltage output to actuators based on the calculation of feedback information from the feedback devices. For instance, based the calculation of the position of the patient support or other parts of the patient positioning system and the comparison of the calculated position with the desired position, the controller may generate a power output to the actuators to adjust the patient support or other parts of the positioning system to the desired position. By way of example, encoders may be coupled to servo motors which operate to rotate the first turret, the second turret, to extend and retract the telescopic arm, and to pivot the arm on the first turret etc. The controller may receive signals from the encoders and calculate the positions of the motors based on the signals received from the encoders. The controller may then generate commands to the servo motors which operate to correct the positions of the turrets, or the arm, or the telescopic arm etc. if they differ from the desired locations. The controller may be programmed to automatically or periodically calibrate the position of the patient support or other parts of the positioning system.

Referring to FIGS. 14-19, a patient support system of this disclosure will now be described. The patient support system can be used with any positioning systems described herein. The patient support system may also be used with any conventional patient positioning systems.

Figure 14A:
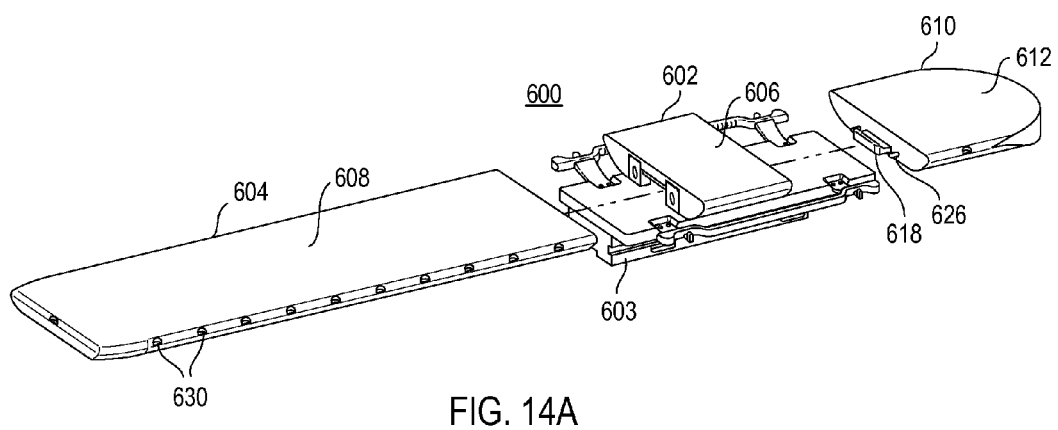
FIGS. 14A-14B illustrate an exemplary patient support system described herein.
Figure 14B:
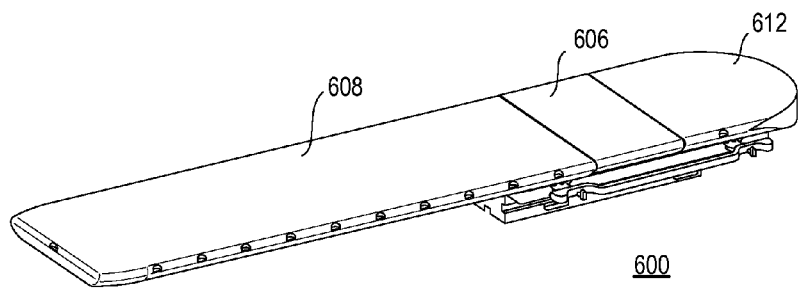

FIG. 14A illustrates an exemplary patient support system 600 of this disclosure. The patient support system 600 includes a first section 602 configured for attachment to a positioning system 603 and a second section 604 removably coupled to the first section 602. Therefore, the first section 602 may provide an interface between the removable second section 604 and a positioning system 603. In some embodiments, the removable second section 604 or at least a portion of the second section 604 may cantilever from a positioning system 603, and the first section 602 may provide support for the second section 604. The first section 602 provides a first support surface 606. The second section 604 provides a second support surface 608. A combined or continuous support surface may be formed when the second section 604 is coupled to the first section 602, as shown in FIG. 14B.

In some embodiments, the patient support system 600 may further include a third section 610 removably coupled to the first section 602, e.g. at a side opposite to the second section 604. The third section 610 provides a third supporting surface 612. A combined or continuous support surface may be formed when the third and the second support sections 610, 604 are coupled to the first section 602, as shown in FIG. 14B.

Figure 15:
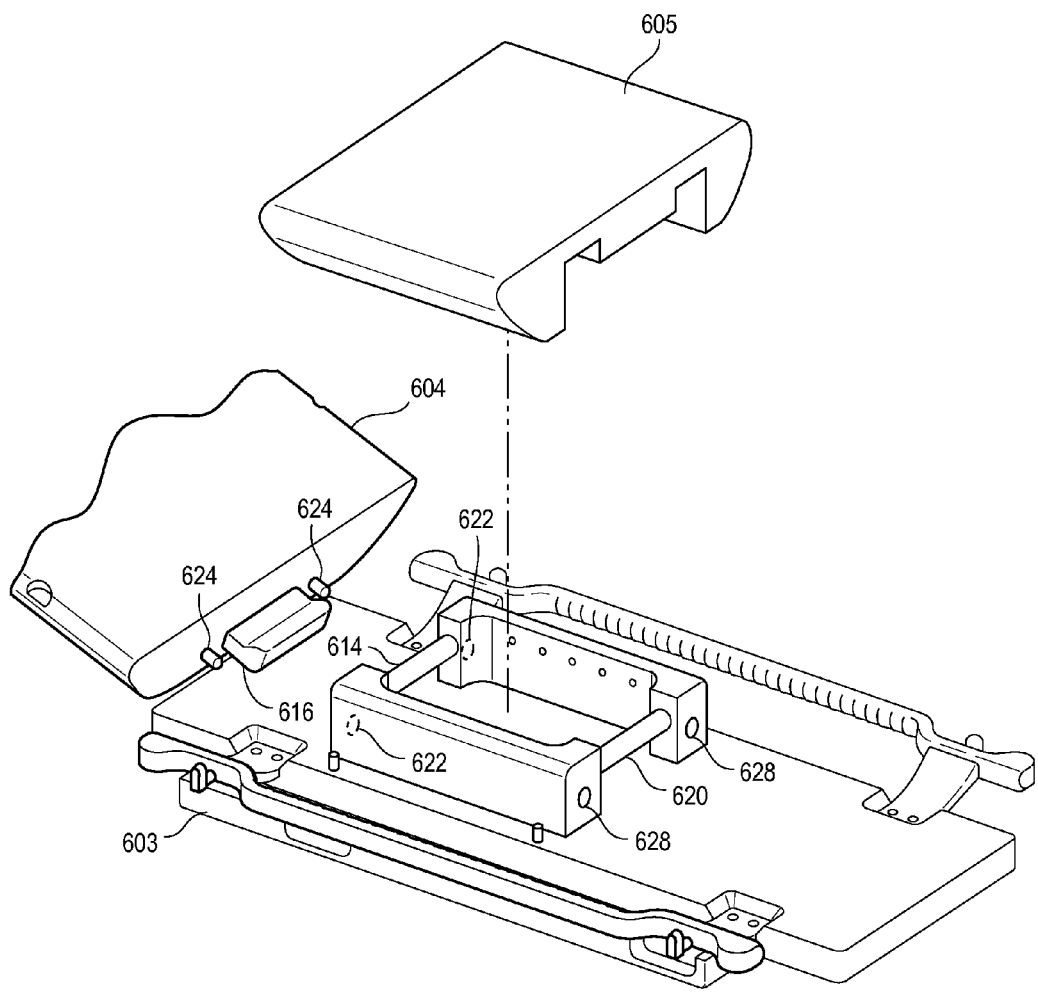
FIG. 15 illustrates an exploded view of an exemplary patient support system described herein.

The patient support system 600 described herein allows quick and easy changing of couch tops in a patient positioning system. The patient support system 600 may include one or more latching mechanisms that facilitate the quick and easy coupling or removing of the second and/or third sections 604, 610. For example, the latching mechanism for the first and second sections 602, 604 may include a first latching member at an end portion of the first section 602 and a second latching member at an end portion of the second section 604. The first and second latching members may be complimentary and engaged when the first and second sections 602, 604 are coupled. FIG. 15 illustrates an exploded view of the first section 602 with a body member 605 being lifted to show the latching mechanism with greater clarity. As shown, the first section 602 includes a first latching member in the form of a bar member 614. The second section 604 includes a second latching member in the form of a hook member 616. The bar member 614 and the hook member 616 may be constructed and configured to be complimentary so that the bar member 614 and hook member 616 may be engaged when the first and the second sections are coupled. Likewise, a hook member 618 may be provided at an end portion of the third section 610 (FIG. 14A) and a bar member 620 may be provided at another end portion of the first section 602, providing a latching mechanism for the third and the first sections 610, 602.

The above description of specific bar and hook members is provided for illustrative purpose. It will be appreciated by one of ordinary skill in the art that other arrangements or latching mechanisms can be used. For instance, a bar member can be arranged in the second section and a complimentary hook member can be arranged in the first section. Other latching mechanisms such as complimentary slots-protrusions etc. can also be used in the patient support system described herein.

The patient support system 600 may also include one or more aligning mechanism for aligning the second section 604 and/or the third section 610 with the first section 602. For example, an aligning mechanism for the first and second sections 602, 604 may include a first aligning member at an end portion of the first section 602 and a second aligning member at an end portion of the second section 604. As shown in FIG. 15, the first section 602 may include a first aligning member in the form of two slots 622. The second section 604 may include a second aligning member in the form of two dowels or protrusions 624. The size, shape, and location of the slots 622 and dowels 624 can be configured so that the protrusions 624 are properly received in the slots 622 when the first and second sections 602, 604 are coupled. Likewise, one or more protrusions 626 may be provided at an end portion of the third section 610 (FIG. 14A) and one or more slots 628 may be provided at another end portion of the first section 602 to provide an aligning mechanism for the third and the first sections 610, 602. It will be appreciated by one of ordinary skill in the art that protrusions can be arranged in the first section 602 and complimentary slots arranged in the second section 604 or third section 610. Other aligning mechanisms can also be used in the patient support system 600 described herein.

Figure 16A:
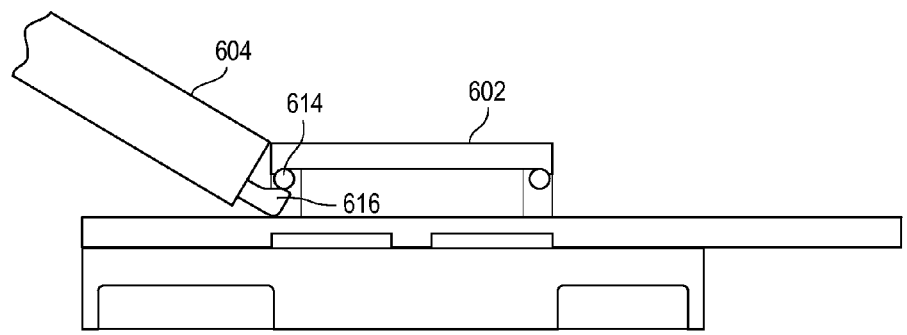
FIGS. 16A-16D illustrate attachment and alignment of a patient support according to some embodiments of the disclosure.
Figure 16B:
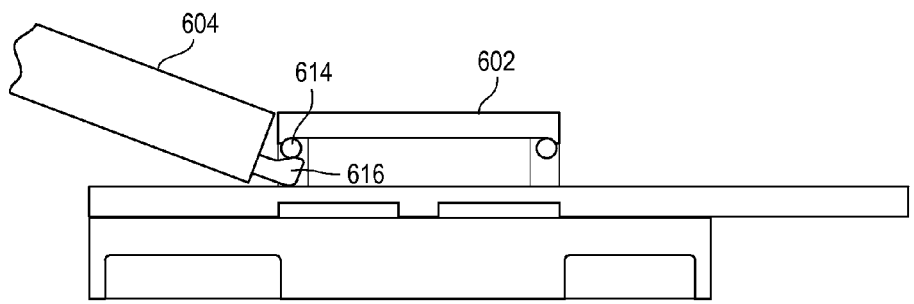
Figure 16C:
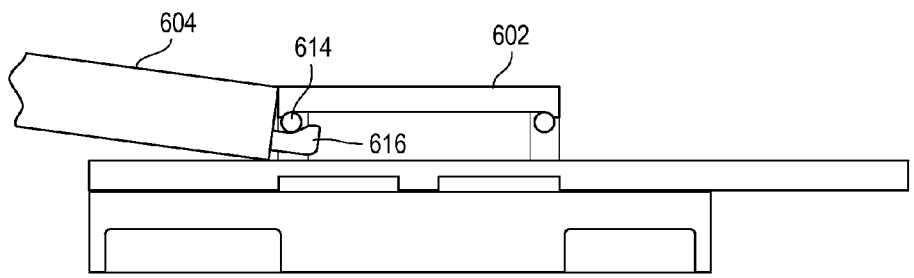
Figure 16D:
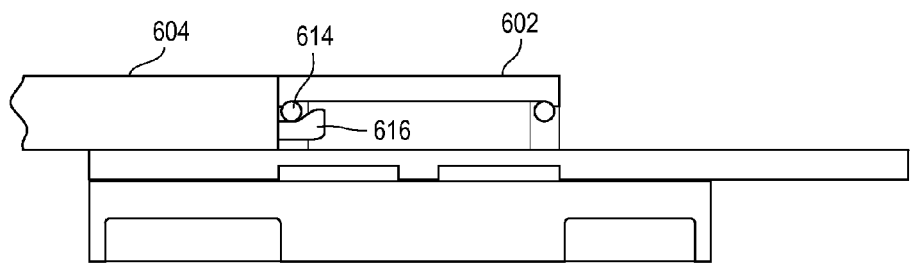

FIGS. 16A-16D illustrate an exemplary embodiment of quick and easy attaching and aligning of a second section 604 with a first section 602 according to this disclosure. In this exemplary embodiment, the first section 602 includes a bar member 614 as a first latching member and two slots 622 (FIG. 15) as a first aligning member. The second section 604 includes a complimentary hook member 616 as a second latching member and two protrusions 624 (FIG. 15) as a second aligning member. The second section 604 can be roughly coupled to the first section 602 by inserting the hook member 616 under the bar member 614 at an oblique angle (FIG. 16A). As the second section 604 lowers, the protrusions 624 in the second section 604 may be received by the slots 622 in the first section 602 and thus accurately align the second section 604 with the first section 602 (FIGS. 16B and 16C). A combined or continuous support surface may be formed once the latching and aligning is complete (FIG. 16D). To detach the second section 604 from the first section 602, an opposite procedure may be performed. No tool is required in attaching the second section 604 to the first section 602, or in removing the second section 604 from the first section 602.

The patient support system 600 may also include a locking mechanism (not shown) for securing the second section 604 to the positioning system 603 once the second section 604 is attached to the first section 602. Various locking mechanisms may be used including such as mechanical latches and magnets etc. Mechanical latches may be used to aid resistance to upward forces of the patient support 604. In cases where the patient support system 600 is used such that the patient weight is generally in the downwards direction, mechanical latches can be omitted to simplify the design and magnets may be used.

Returning to FIGS. 14A and 14B, the patient support system 600 or at least the second section 604 or the third section 610 may include index features 630. For example, a plurality pairs of indexed notches or recesses 630 may be provided along the longitudinal sides of the second section 604. The notches or recesses 630 may be configured for receiving a locking member e.g. an elongate bar member (not shown) to which a restraining or immobilization device may be secured. With the index features 630, various immobilization devices or accessories may be accurately secured to the patient support system 600 for repeated treatments or imaging of patients.

The patient support system may include a detection system (not shown) which may be configured to identify the type of the couch top coupled to the first section. One or more load cells (not shown) may also be provided in the patient support system to measure a weight and center of gravity of the patient support.

The first, second, or third sections of the patient support may be constructed from any suitable materials. By way of example, at least the second and/or third sections 604, 610 may be constructed from a material that includes carbon fiber composites, methacrylate plastics, solid foams of various materials, or aerogels etc. In some embodiments, at least the second and/or the third sections 604, 610 may be constructed from a material comprising carbon fiber. In some embodiments, at least the second and/or the third sections 604, 610 may be constructed solid from a material such as carbon fiber. In some embodiments, at least the second and/or third sections 604, 610 may be constructed having a hollow interior with its outer surface reinforced with a thin and strong material such as carbon fiber. In some embodiments, the hollow interior may be optionally filled with light materials such as foam. For imaging procedures, the second and/or third sections 604, 610 of the patient support may be constructed from a material that transmits radiation or has low radiation attenuation coefficients.

Figure 17A:
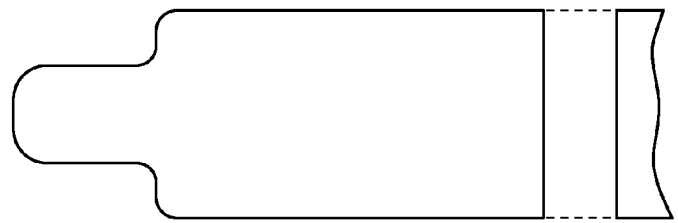
FIGS. 17A-17C illustrate exemplary couch tops which can be quickly and easily attached to and removed from the patient support system described herein.
Figure 17B:
Figure 17C:
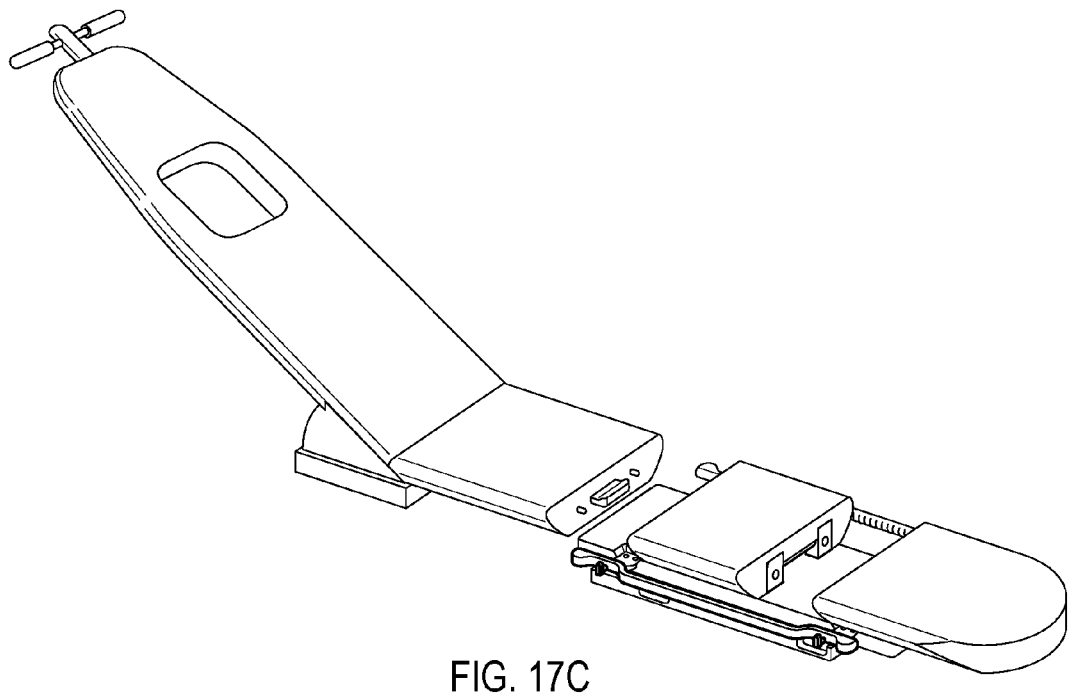

The capability of quick and easy changing of couch tops allows quick and easy transition between different treatment procedures or between treatment and imaging procedures. Various couch tops may therefore be customarily designed and made for various treatment or imaging procedures and used in conjunction with the support system described herein. By way of example, FIG. 17A illustrates an exemplary patient support configured for stereotactic radiotherapy (SRS). FIG. 17B illustrates an exemplary patient support for brachytherapy. FIG. 17C shows that the removable couch top may further include multiple adjustable segments and may be configured to support a patient in a sitting, leaning, or other suitable position. Indeed, the patient support system described herein may be used with various couch tops which may include various accessories or features to secure or immobilize the patient.

Figure 18A:
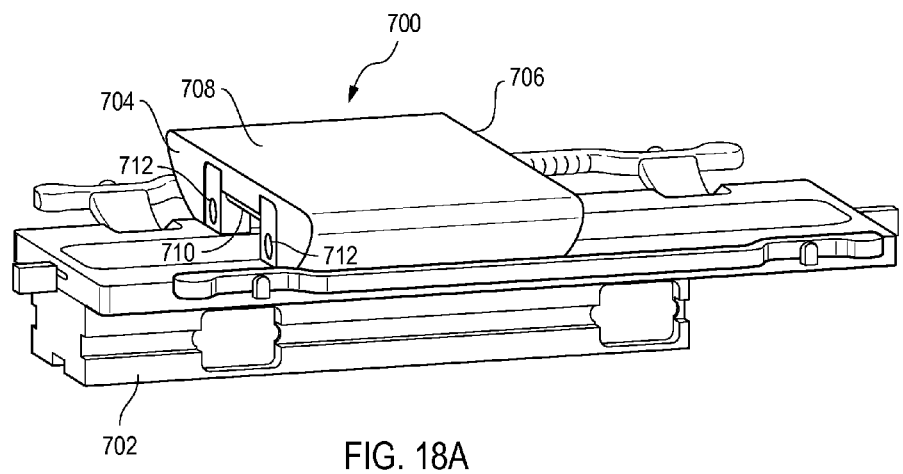
FIGS. 18A-18B illustrate an exemplary interface structure described herein.
Figure 18B:
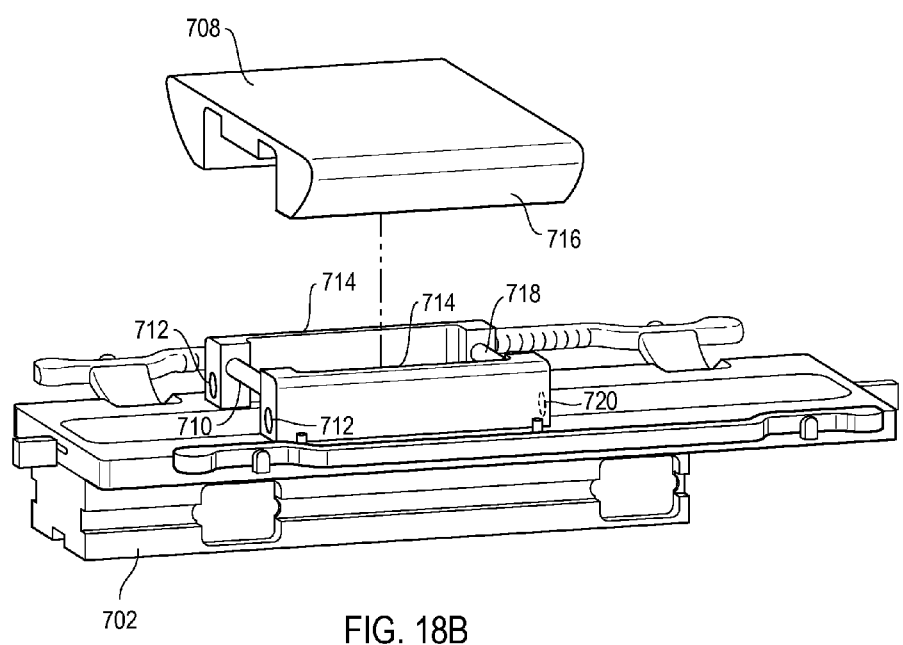

FIGS. 18A-18B illustrate an exemplary interface structure 700 according to some embodiments of this disclosure. The interface structure 700 is adapted for attachment to a patient positioning system 702 for interfacing a removable patient support with the patient positioning system 702. As shown in FIG. 18A, the interface structure 700 may have a first end 704, a second end 706, and a support surface 708 between the first and the second ends 704, 706. The interface structure 700 may include a first latching member 710 at the first end 704 for removably coupling a first patient support. The interface structure 700 may also include a first aligning member 712 at the first end 704 for aligning the first patient support with the interface structure 700. The first patient support and interface structure 700 may provide a combined or continuous support surface once the first patient support and the interface structure 700 are attached. As shown in FIG. 18B, the interface structure 700 may also include a second latching member 718 at the second end 706 of the interface structure 700 for removably coupling a second patient support. The interface structure 700 may also include a second aligning member 720 at the second end 706 of the structure 700 for aligning a second patient support with the structure 700. A combined support surface may be formed once the first patient support, the structure, and the second patient support are attached.

As shown in FIG. 18B, the interface structure 700 may include a pair of elongate supports 714 each having a first end portion and a second end portion. The pair of elongate supports 714 may be attached to the positioning system 702 generally in parallel. The first bar member 710 may be coupled to each of the first end portions of the elongate supports 714. One or more slots 712 may be provided at one or both of the first end portions of the elongate supports 714. A body member 716 may be placed above the elongate supports 714 and the first bar member 710. The body member 716 provides a support surface 708 of the interface structure 700. In some embodiments, a second bar member 718 may be coupled to each of the second end portions of the elongate supports 714. One or more slots 720 may be provided at one or both of the second end portions of the elongate supports 714.

Figure 19:
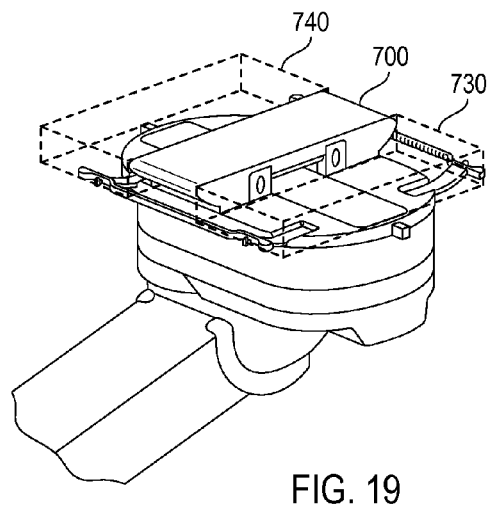
FIG. 19 illustrates an exemplary interface structure and end blocks according to some embodiments of the disclosure.

Advantageously, the interface structure 700 may be used with various existing patient positioning systems and allows quick and easy coupling and removing couch tops. For example, various couch tops may be designed and constructed to have complimentary latching and aligning members for coupling and aligning with the interface structure 700 as described above. Furthermore, the interface structure 700 may also be used with existing couch tops to provide backward compatibility. FIG. 19 shows a first-end block 730 and a second-end block 740 which may be placed at both ends of the interface structure 700. The end blocks 730, 740 may be configured to form a combined support structure with the interface structure 700. Existing couch top may then be placed on top of the combined support structure and used to support a patient. While the end blocks would raise the minimal height of the couch, it would support existing couch tops as a compromise.

Figure 20:
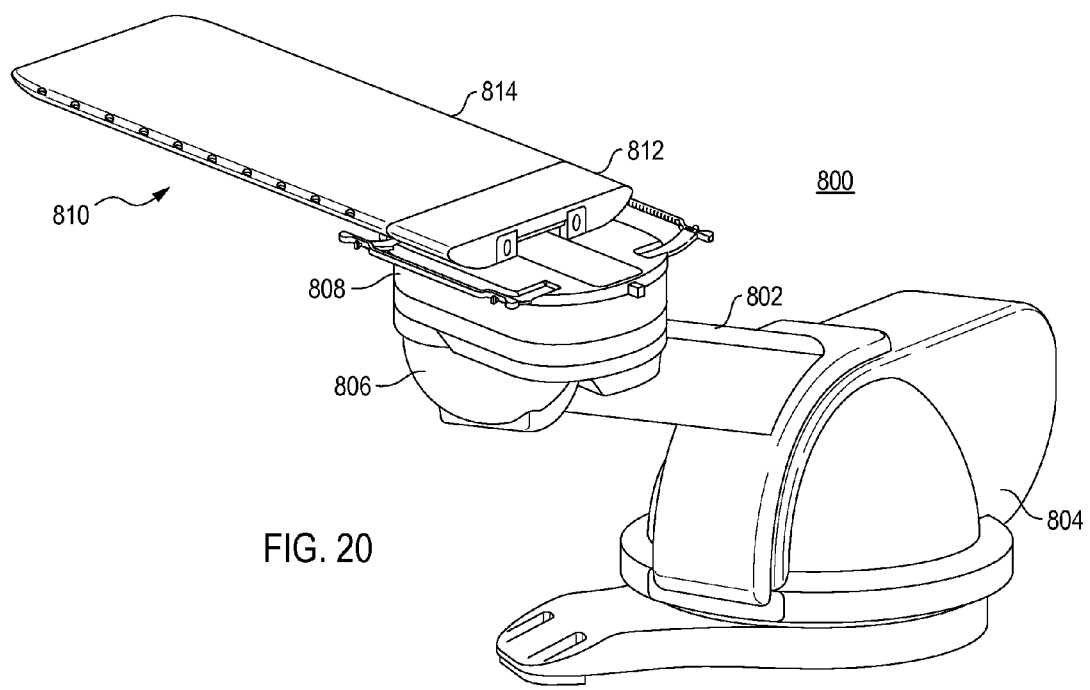
FIG. 20 illustrates an exemplary patient positioning system described herein.

FIG. 20 illustrates an exemplary positioning system 800 that includes a patient support system and patient positioning devices described herein. The positioning system 800 may include an arm 802, a first turret 804 coupled to a first end portion of the arm 802, a second turret 806 coupled to a second end portion of the arm 802, and a carriage 808 coupled to the second turret 806. A patient support 810 may be coupled to the carriage 808. The patient support 810 may include a first section 812 configured for attachment to the carriage 808 and a second section 814 removably coupled to the first section 812. The patient support 810 may include a latching mechanism for quick and easy coupling of the second section 814 to the first section 812 or removing of the second section 814 from the first section 812, as described in greater details above. The patient support 810 may also include an aligning mechanism for accurate aligning of the second section 812 with the first section 814, as described in greater details above. The patient support 810 may also include a third section (not shown) which may be coupled to the first section 812 at the opposite side of the second section 814. The first turret 804, the second turret 806, the arm 802, and the carriage 808 may operate to move the patient support 810 in various degrees of freedom, as described in greater details above.

Embodiments of patient positioning systems and patient support systems are described. Those skilled in the art will appreciate that various modifications may be made within the spirit and scope of the disclosure. All these or other variations and modifications are contemplated by the inventors and within the scope of the disclosure.

What is claimed is:

1. A patient positioning system, comprising:
   an arm having a first portion and a second portion;
   a first positioning device coupled to the first portion of the arm, the first positioning device providing support for the arm and rotatable on a first axis, thereby allowing the arm to rotate with the first positioning device;
   a second positioning device coupled to the second portion of the arm, the second positioning device being operable to rotate a patient support at least on a second axis;
   a third positioning device coupled to the arm and operable to extend and/or retract the second portion of the arm relative to the first portion of the arm along a longitudinal axis of the arm; and
   a control system coupled to the first, the second, and/or the third positioning devices to control operations of the first, the second, and/or the third positioning devices,
   wherein the first positioning device is operable to pivot the arm on a third axis.

2. A patient positioning system comprising
   an arm having a first portion and a second portion, the second portion of the arm being telescopic relative to the first portion of the arm;
   a first positioning device coupled to the first portion of the arm, the first positioning device providing support for the arm and rotatable on a first axis, thereby allowing the arm to rotate with the first positioning device; and
   a second positioning device coupled to the second portion of the arm and movable with the second portion of the arm relative to the first portion of the arm, the second positioning device being operable to rotate a patient support at least on a second axis;
   wherein the first positioning device is operable to pivot the arm on a third axis.

3. The patient positioning system of claim 2 wherein the arm is non-articulated.

4. The patient positioning system of claim 2 further comprising a movable base member, the movable base member being coupled to the first positioning device thereby allowing the first positioning device to further move with the movable base member.

5. A patient positioning system comprising
   an arm having a first portion and a second portion, the second portion of the arm being telescopic relative to the first portion of the arm;
   a first positioning device coupled to the first portion of the arm, the first positioning device providing support for the arm and rotatable on a first axis, thereby allowing the arm to rotate with the first positioning device; and
   a second positioning device coupled to the second portion of the arm and movable with the second portion of the arm relative to the first portion of the arm, the second positioning device being operable to rotate a patient support at least on a second axis;
   wherein the second positioning device is further operable to rotate the patient support on at least one additional axis that is different from the second axis.

6. The patient positioning system of claim 5 wherein the second positioning device comprises a wrist assembly that is operable to rotate the patient support on a yaw, a pitch, and a roll axis.

7. A patient positioning system comprising
   an arm having a first portion and a second portion, the second portion of the arm being telescopic relative to the first portion of the arm;
   a first positioning device coupled to the first portion of the arm, the first positioning device providing support for the arm and rotatable on a first axis, thereby allowing the arm to rotate with the first positioning device; and
   a second positioning device coupled to the second portion of the arm and movable with the second portion of the arm relative to the first portion of the arm, the second positioning device being operable to rotate a patient support at least on a second axis;
   wherein the first positioning device is enclosed in an enclosure in a form comprising a portion of sphere.

8. The patient positioning system of claim 7 wherein at least a portion of the first portion of the arm is enclosed in the enclosure.

9. A patient positioning system comprising
   a first turret rotatable on a first axis;
   an arm having a first end portion and a second end portion, the first end portion of the arm being coupled to the first turret, thereby allowing the arm to be supported by and rotate with the first turret; and
   a second turret coupled to the second end portion of the arm and rotatable on a second axis, the second turret being adapted to couple with a patient support to allow the patient support to rotate with the second turret.

10. The patient positioning system of claim 9 wherein the arm is telescopic.

11. The patient positioning system of claim 10 wherein the arm is pivotable about the first turret on a third axis.

12. The patient positioning system of claim 11 wherein the arm is non-articulated.

13. The patient positioning system of claim 9 wherein the arm is pivotable about the first turret on a third axis.

14. The patient positioning system of claim 13 wherein the arm is non-articulated.

15. The patient positioning system of claim 9 wherein the arm is non-articulated.

16. The patient positioning system of claim 9 wherein the second axis is generally perpendicular to the first axis.

17. The patient positioning system of claim 9 further comprising a movable base member, wherein the movable base member is coupled to the first turret thereby allowing the first turret to further move with the movable base member.

18. The patient positioning system of claim 17 further comprising a carriage between the second turret and the patient support, the second turret being operable to rotate the carriage on an axis that is different from the second axis, thereby allowing the patient support to rotate with the carriage.

19. The patient positioning system of claim 18 wherein the carriage is operable to pitch and/or roll the patient support.

20. A patient positioning system, comprising:
    an arm having a first portion and a second portion;
    a first positioning device coupled to the first portion of the arm, the first positioning device providing support for the arm and rotatable on a first axis, thereby allowing the arm to rotate with the first positioning device;

a second positioning device coupled to the second portion of the arm, the second positioning device being operable to rotate a patient support at least on a second axis;
a third positioning device coupled to the arm and operable to extend and/or retract the second portion of the arm relative to the first portion of the arm along a longitudinal axis of the arm; and
a control system coupled to the first, the second, and/or the third positioning devices to control operations of the first, the second, and/or the third positioning devices, wherein each of the first, second, and third positioning devices comprises one or more servo motors and one or more feedback devices which are coupled to the controller.

21. The patient positioning system of claim 20 wherein the control system comprises a controller and a user interface device which allows a user to interact with the controller in controlling the operations of the first, second, and/or third positioning devices.

22. The patient positioning system of claim 21 wherein the user interface device comprises a remote control unit that allows the user to remotely control the operations of the first, second, and/or third positioning devices.

23. The patient positioning system of claim 20 further comprising a movable base member, wherein the movable base member is coupled to first positioning device thereby allowing the first positioning device to further move with the movable base member, and wherein the control system is further coupled to the movable base member for controlling the movable base member.

24. The patient positioning system of claim 20 wherein the controller is configured to control the first, second, and/or third positioning device based on at least signals received from the one or more feedback devices.

25. A patient positioning system, comprising:
an arm having a first portion and a second portion;
a first positioning device coupled to the first portion of the arm, the first positioning device providing support for the arm and rotatable on a first axis, thereby allowing the arm to rotate with the first positioning device;
a second positioning device coupled to the second portion of the arm, the second positioning device being operable to rotate a patient support at least on a second axis;
a third positioning device coupled to the arm and operable to extend and/or retract the second portion of the arm relative to the first portion of the arm along a longitudinal axis of the arm; and
a control system coupled to the first, the second, and/or the third positioning devices to control operations of the first, the second, and/or the third positioning devices,
wherein the second positioning device comprises a wrist assembly which is operable to rotate the patient support on a yaw, a pitch, and a roll axis.

26. A patient positioning system, comprising:
an arm having a first portion and a second portion;
a first positioning device coupled to the first portion of the arm, the first positioning device providing support for the arm and rotatable on a first axis, thereby allowing the arm to rotate with the first positioning device;
a second positioning device coupled to the second portion of the arm, the second positioning device being operable to rotate a patient support at least on a second axis;
a third positioning device coupled to the arm and operable to extend and/or retract the second portion of the arm relative to the first portion of the arm along a longitudinal axis of the arm; and
a control system coupled to the first, the second, and/or the third positioning devices to control operations of the first, the second, and/or the third positioning devices,
wherein the first positioning device is enclosed in an enclosure in a form comprising a portion of sphere.

27. The patient positioning system of claim 26 wherein at least a portion of the first portion of the arm is enclosed in the enclosure.

28. A method comprising:
providing a patient positioning system;
positioning a patient using the patient positioning system in a first medical system;
transporting the patient using the patient positioning system from the first medical system to a second medical system; and
positioning the patient using the patient positioning system in the second medical system;
wherein the patient positioning system comprises:
an arm having a first portion and a second portion, the second portion of the arm being telescopic relative to the first portion of the arm;
a first positioning device coupled to the first portion of the arm, the first positioning device providing support for the arm and rotatable on a first axis, thereby allowing the arm to rotate with the first positioning device; and
a second positioning device coupled to the second portion of the arm and movable with the second portion of the arm relative to the first portion of the arm, the second positioning device being operable to rotate a patient support at least on a second axis.

29. The method of claim 28 wherein the first medical system and the second medical system are located in a same room.

30. The method of claim 29 wherein the first medical system and the second medical system are separable by a shielding structure.

31. The method of claim 28 wherein the first medical system is a radiation therapy system and the second medical system is a medical imaging system.

32. The method of claim 31 wherein the second medical system is a magnetic resonance imaging (MRI) system or X-ray imaging system.

33. The method of claim 28 wherein the first medical system is a medical imaging system and the second medical system is a radiation therapy system.

34. The method of claim 28 wherein the first medical system and the second medical system are independently a medical imaging system.

35. The method of claim 28 wherein the first medical system and the second medical system are located in different rooms.

* * * * *